United States Patent [19] [11] 4,102,884
Kruger [45] Jul. 25, 1978

[54] 14 β-HYDROXY 3-DEOXYCARDENOLIDES

[75] Inventor: Gunther Kruger, St. Laurent, Canada

[73] Assignee: Steele Chemicals Co. Ltd., Pointe Claire, Canada

[21] Appl. No.: 683,843

[22] Filed: May 5, 1976

[30] Foreign Application Priority Data

May 7, 1975 [GB] United Kingdom ............... 19144/75

[51] Int. Cl.² ............................................. C07J 17/00
[52] U.S. Cl. ................................................ 260/239.57
[58] Field of Search ................................... 260/239.57

[56] References Cited
U.S. PATENT DOCUMENTS 3,087,944 4/1963 Rubin ............................... 260/397.45
3,952,030 4/1976 Chambers et al. ................ 260/397.4
3,981,982 9/1976 Oslapas et al. ................... 260/239.57

Primary Examiner—Elbert L. Roberts

Attorney, Agent, or Firm—McFadden, Fincham & Co.

[57] ABSTRACT

Novel compounds of the formula

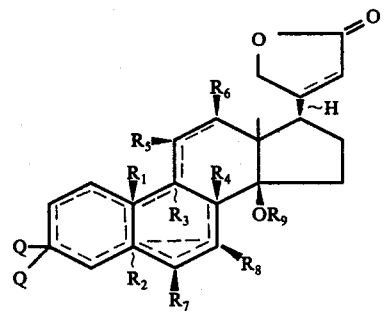

useful as pharmaceutical compounds are disclosed. Processes are also disclosed for their preparation.

51 Claims, No Drawings

14 β-HYDROXY 3-DEOXYCARDENOLIDES

The present application relates to 3-deoxy 14β-hydroxy cardenolides, and their 19-nor analogs, having additional functionalities, such as 19- and β-hydroxy groups and their derivatives, double bonds and keto groups in the A,B,C ring system; methods of their preparation from 3,14β-dihydroxy cardenolides via the corresponding 3-ketones; deoxygenation methods for the deoxygenation of 3-keto steroids, which do not belong to the class of 14β-hydroxy cardenolides; methods for the preparation of 16-dehydro-20α-hydroxy steroids from 16-dehydro-20-keto steroids; and a method for introducing tritium and deuterium into the 3, 5 and 20-position of steroids.

3-Deoxydigitoxigenin, which has a saturated A- and B-ring, has been prepared by

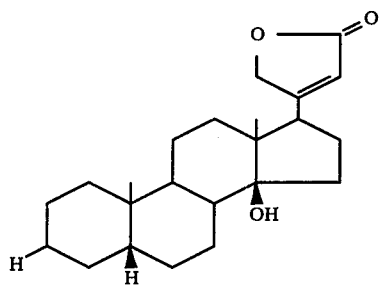

1. T. R. Witty, W. R. Remers and H. R. Besch, J. Pharmaceut. Sci., 64, 1248 (1975); these authors also prepared the 20(22)-dihydro analog, the 2,3- and 3,4-dehydro analog and the 3,4-oxido analog of 3-deoxydigitoxigenin.
2. Y. Saito, Y. Kanemasa and M. Okada, Chem. Pharm. Bull. (Tokyo), 18, 629 (1970); these authors also prepared the 2,3- and 3,4-dehydro analog of 3-deoxydigitoxigenin; their method was used by T. R. Witty et al.
3. W. Zurcher. E. Weiss-Berg and Ch. Tamm, Helv. Chim. Acta, 52, 2449 (1969).

No other 3-deoxy 14β-oxygenated cardenolides with saturated A- and B-rings appear to have been prepared.

Well known (cf. L. F. Fieser and M. Fieser, "Steroids", Reinhold Publishing Corp., New York, 1967) is the 3,5-diene scillaridin A

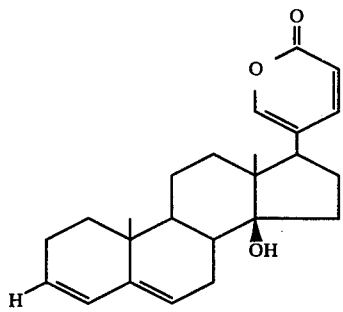

of the related bufadienolide series. The diene, which has no oxygen atom in the 3-position is obtained by acid treatment of scillaren A

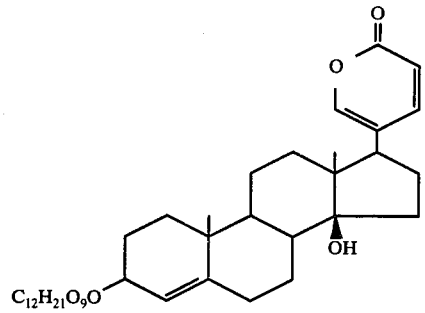

The above diene would be expected to be less useful for the preparation of the corresponding tetrahydro analog, which has saturated A- and B-rings, than the 3-enes of this invention as taught hereinbelow, since the double bond in position 3 is much more readily hydrogenated than that in position 5, so that the hydrogenation of the α-pyrone ring in the bufadienolide and loss of physiological activity would be likely.

In the prior art, the preparation of 3-deoxydigitoxigenin from digitoxigenin as carried out by Y. Saito et al (cited above) and subsequently by T. R. Witty et al (cited above) takes place in 3 steps and starts with digitoxigenin:

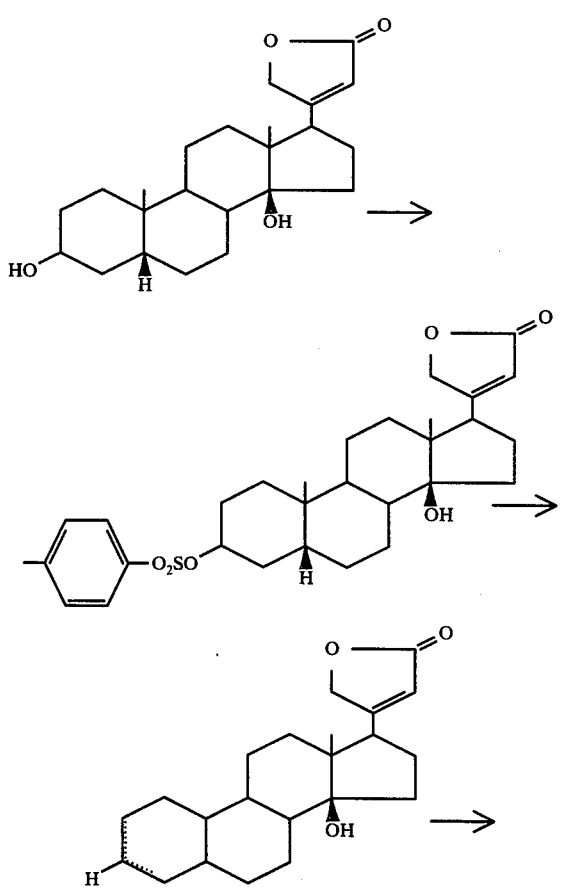

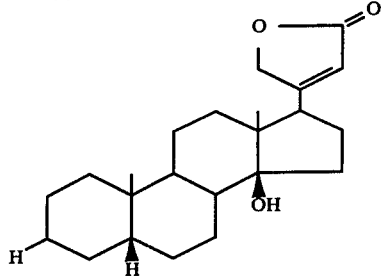

3-Deoxydigitoxigenin is obtained in less than 20% yield and involves a chromatographic purification. The preparation of W. Zürcher et al proceeds in even smaller yield and the purification of the intermediates is more laborious, e.g., it entails 2 chromatographic purifications. It proceeds as follows:

digitoxigenin ⟶

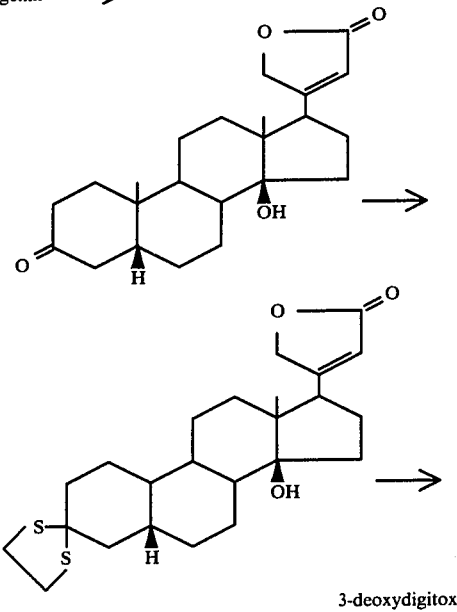

3-deoxydigitoxigenin

Also, in the prior art, most of the oxidations of the aglycones to the corresponding 3-keto cardenolides described in the literature appear to have been carried out by oxidation with molecular oxgyen in presence of platinum (see, for example S. M. Kupchan, M. Mokotoff, R. S. Saudku and L. E. Hokin, J. Med. Chem. and Ch. Tamm and A. Gubler, Helv. Chim. Acta, 42, 239 (1959), who describe the oxidation of strophanthidol and of digoxigenin, respectively, by Pt/O₂; see also P. J. Neustaedter in "Steroid Reactions" editor C. Djerassi, Holden-Day, Inc., 1963, pp. 126–128).

Recently 14,19-dihydroxy-3-oxo-carda-4,20(22)dienolide has been prepared by oxidation of strophanthidol with N-bromoacetamide and separation of the ketonic from the non-ketonic products via derivatization with Girards T and subsequent treatment of the Girards T derivatives with aqueous hydrochloric acid (V. N. Gupta and M. Ehrenstein, Can. J. Chem., 46, 2601 (1968). "Steroid Reactions" cited above, p. 120 lists the oxidation of strophantidol and of gitoxigenin to the corresponding 3-keto analogs by means of N-bromoacetamide in the presence of pyridine and T-butanol. 14β-Hydroxy-3-oxocardenolides have also been obtained in partial syntheses via the corresponding 14-enes from cheap bulk steroids (W. Fritsch, V. Stache, W. Haede, K. Radscheit and H. Ruschig, Liebigs Ann. Chem. 721, 168 (1969)).

Processes of the prior art used for the deoxygenation of 3-keto steroids which are not 14β-hydroxy cardenolides and for the reduction of 16-dehydro-20-keto steroids by zinc are as follows.

3-Keto steroids have been deoxygenated in the past by zinc in conjunction with hydrochloric acid, dry hydrogen chloride, chlorotrimethylsilane and acetic acid.

The deoxygenation of ketones with a mineral acid especially with hydrochloric acid and zinc is known in synthetic organic chemistry as the Clemmensen reduction. In a typical Clemmensen reduction half-concentrated to concentrated hydrochloric acid, amalgamated zinc and a water immiscible co-solvent such as toluene are employed (see for example E. Vogel, Practical Organic Chemistry, 3rd edition, Longmans, London, 1966, pp. 728 and 738).

Thus the steroid cholest-4-en-3-one has been reduced by a typical Clemmensen reduction, employing 7N hydrochloric acid as the mineral acid. After refluxing of the reaction mixture work up and chromatographic purification, 5β-cholest-3-ene was obtained (see B. R. Davies and P. D. Woodgate, J. Chem. Soc. (C), 1966, 2006).

Recently it has been reported (see M. Toda and Y. Hirata, J. Chem. Soc., Chem. Commun., 1969, 919) that keto steroids can be deoxygenated with zinc, which has been activated by treatment with dilute hydrochloric acid, and dry hydrogen chloride at 0° C. in presence of an organic solvent, preferably anhydrous ether. 3-Keto and 17-keto groups are non-selectively deoxygenated by this method.

The method which employs chlorotrimethylsilane and zinc yields olefins from saturated ketones (see for example W. B. Motherwell, J.C.S. Chem. Commun., 1973, 935 and P. Hodge and M. N. Khan, J.C.S., 1975, 809).

It will be noted that a large amount of acetic acid is used (see J. McKenna, J. K. Norymberski and R. D. Stubbs, J.C.S., 1959 2502; J. K. Norymberski, J.C.S., 1956, 517; A. Bowers, A. D. Cross, J. A. Edwards, H. Carpio, M. C. Calzada and E. Denoit, J. Med. Chem., 6, 156 (1963); A. Crastes de Paulet, J. Bascoul, Bull. Soc., 1969, 939; and Fieser and Fieser, Reagents for Organic Synthesis, Vol. 1, cited above, p. 1278). In the published deoxygenation procedures 4-dehydro-3-keto steroids have been converted to reduction products from which predominantly 3-dehydro 5α-hydrogen steroids and lesser amounts of the 5β-hydrogen isomers were isolated. The isomers are difficult to separate and in some experiments only the 5α-isomers were isolated. The deoxygenation of a 5(6)-dehydro-7-ketone to small amounts of a 5α-hydrogen 6-ene is also described. The method has not found use in the deoxygenation of saturated ketones.

A 16-dehydro-20-ketone has previously been converted in low yield to 16-dehydro-20α-alcohols, besides the saturated 16,17-dihydro-20-ketone, by treatment with zinc powder in acetic acid at 100°. (See A. Ercoli, P. De Ruggieri, Farm. Sci. e tec (Pavia), 7, 11 (1952); C. A. 46, 10186 (1952); see also reference 16 of J. McKenna, J. K. Norymberski and R. D. Stubbs).

In one aspect of the invention, there are provided compounds of the formula

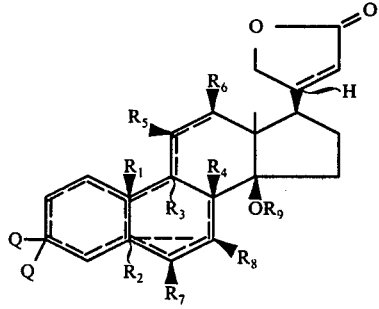
(I)

wherein Q is selected from the group consisting of hydrogen, deuterium or tritium; $R_1$ is selected from the group consisting

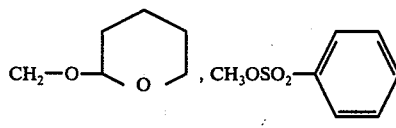

of $CH_2OH$, $CH_2OCH$, $CH_2OCCH_3$, $CH_2OCCF_2CF_2CF_3$, $CH_2OCC(CH_3)_3$, $CH_2OCCH_2CO_2H$, $CH_2OC(CH_2)_2CO_2H$,

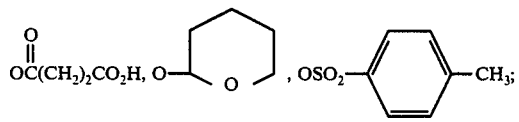

CHO, $CH_2F$, $CH_2Cl$, $CH_2Br$, $CH_2I$, $CH_3$, $CO_2H$, $CO_2CH_3$, OH, H; $R_2$ is selected from the group consisting of β-H, β-deuterium, β-tritium, α-H, α-deuterium, α-tritium, β-OH; $R_3$ is selected from the group consisting of α-H, β-H, β—OH; $R_4$ is selected from the group consisting of β-H, β—OH; $R_5$, $R_6$, $R_7$, $R_8$ are selected from the group consisting of H, = O,

OH, OCH, OCCH$_3$, OCCF$_2$CF$_2$CF$_3$, OCC(CH$_3$)$_3$, OCCH$_2$CO$_2$H,

OC(CH$_2$)$_2$CO$_2$H, O—⟨tetrahydropyranyl⟩, OSO$_2$—⟨C$_6$H$_4$⟩—CH$_3$;

$R_9$ is selected from the group consisting of H, $CH_3—\overset{O}{\underset{\|}{C}}—$, $H\overset{O}{\underset{\|}{C}}—$;

and wherein the dotted lines represent additional bonds present in a number of the individual compounds; in the case of compounds having an additional bond at the 5,8,9 or 10-position the substituents $R_2$, $R_4$, $R_1$ or $R_3$ respectively, are absent; with the wavy lines between the steroid nucleus and some of the substituents indicating that the latter may be present in some compounds in one and in other compounds in the other of the two sterically possible positions; in the case of $R_1 = CH_3$ and of the absence of additional bonds, $R_1$, $R_2$, $R_3$, $R_4$, $R_5$ or $R_6$ are OH, or $R_5$ or $R_6$ are O=; most of the compounds are card-20(22)-enolides rather than the saturated cardenolides; i.e. most of the compounds have a double bond between the 20- and 22-position.

The 3-deoxy steroid prepared from 3-keto steroids by the processes of the present invention are those compounds having the formula

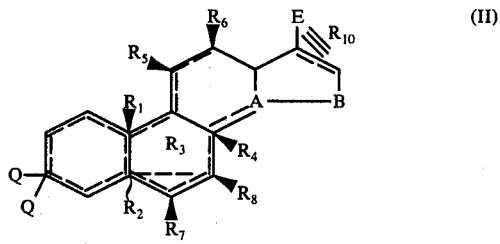
(II)

wherein Q, $R_1$ through $R_8$, and also the dotted and wavy lines are as defined in formula I; $R_{10}$ is selected from H, OH and $\overset{O}{\underset{\|}{OC}}—CH_3;$ and wherein E is selected from the group consisting of

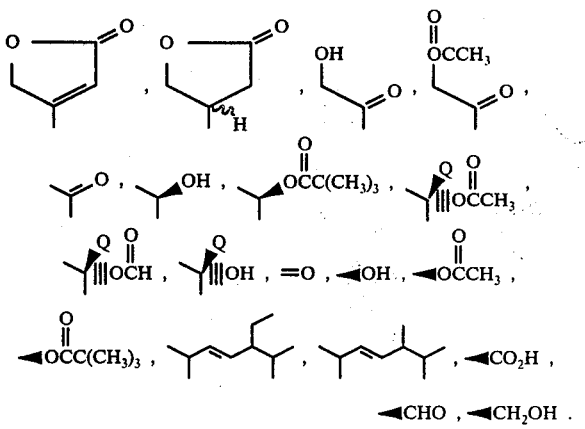

and wherein A—B = C(β—OH)—CH$_2$,

C(β—OCCH$_3$)—CH$_2$, C(β—OCH)—CH$_2$,

C=CH, C(α—OH)—CH$_2$, C(β—OH)-CHBr, C(β—H)—CH$_2$, C(α—H)—CH$_2$,

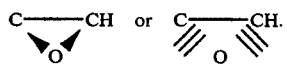

The compounds of the present invention are 14β-hydroxy cardenolides and in contrast to the steroids of natural origin, they do not carry an oxygen function in the 3-position. In further contrast to the cardenolides of natural origin, they comprise compounds not having a 19-methyl group. They also comprise compounds having oxygen functions, especially hydroxy groups on the β-side of the B- and C-ring and at the angular 19-carbon atom of the steroid molecule, in addition to the 14β-hydroxy group. They further comprise compounds having double bonds in the A, B and C-ring and keto groups in the latter ring.

The 3-deoxy 14β-hydroxy cardenolides of this invention are prepared from the aglycones, which may be referred to as genins, of naturally occurring 14β-hydroxy cardenolides which have a glycosyloxy group in the 3-position by oxidation of the liberated 3-hydroxy group to the corresponding 3-ketones and subsequent deoxygenation of the latter. In the case that the aglycones have a hydroxy group in position 5, the 5-hydroxy 3-ketone formed by the oxidation may be dehydrated to the corresponding 4-en-3-one. The latter may then be deoxygenated or may be first converted to the corresponding saturated 3-ketone, which then is deoxygenated.

Because the labile 14β-hydroxy butenolide moiety, as well as other functionalities which may be present in the aglycones, general methods described in the literature for the oxidation of alcohols to ketones and the deoxygenation of the latter are not generally applicable to the conversion of the aglycones to 3-keto and 3-deoxy analogs. The oxidation of the genins, which are 3,14β-dihydroxy cardenolides, to the 3-oxo-14β-hydroxy cardenolides may be brought about by oxidation with molecular oxygen in presence of platinum. Preferably it may be brought about by oxidation with N-bromoacetamide under the special conditions of this invention. The dehydration of the 5-hydroxy-3-ketones may be brought about by treatment with a carboxylic or mineral acid, preferably a mineral acid such as hydrochloric acid.

The deoxygenation of the 3-oxo-14β-hydroxy cardenolides may be brought about in low yield by the method used for the conversion of digitoxigenin to 3-deoxydigitoxigenin, in which the keto group is converted to the thioketal which is then desulfurated by Raney nickel. Preferably it may be brought about by treatment with zinc and a carboxylic acid under the special conditions of this invention. It may also be brought about by conversion of the 3-keto group into the corresponding tosylhydrazone and subsequent treatment of the latter with a hydride, e.g. sodium borohydride or sodium cyanoborohydride.

In detail, the preferred method of oxidation is carried out by treatment of the genin with 0.5 to 2.5 parts, preferably 1.0–1.4 parts, of N-bromoacetamide in aqueous tertiary butylalcohol at temperatures between $-10°$ and $50°$ C, preferably at room temperature, for an optimal period of time ranging from 0.5 hrs. to 10 days. The time to bring the oxidation effectively to completion depends greatly on the kind of the genin used as the starting material. For example, in the case of the oxidation of digoxin, digitoxin, and strophanthidin with 1.2 parts of N-bromoacetamide at room temperature to the analogous 3-ketones, these periods of time range from 60–100 minutes, 80–120 minutes and 48–56 hrs., respectively, while for the effective oxidation of digoxigenin to the corresponding 3,12-diketone more than 96 hours, i.e. 4 days, are required.

The reactions preferably are carried out in the dark. In the case of the oxidation of strophanthidin to the corresponding 3-ketone, i.e. strophanthidone, the rigorous exclusion of light is especially important. The oxidation of strophanthidin by N-bromoacetamide to the corresponding 3-oxo-19-carboxylic acid, which can readily be converted to 3-oxo-19-norcarda-5(10),20(22)-dienolide, can be effected by exposing the reaction mixture, containing strophanthidone, to daylight for several hours at room temperature.

The 5-hydroxy 3-ketones, such as strophanthidone, obtained by the oxidation of those aglycones, which are 3,5,14-thiols, are converted to the corresponding 4-en-3-ones by treatment with a carboxylic acid, preferably acetic acid, at elevated temperatures ranging from $60°$ to $120°$ C, preferably between $65°$ and $85°$ C for 1 to 20 hours, depending on the temperature. One to one hundred, preferably 1–5 parts of acid may be employed and it is advantageous to employ a co-solvent, such as an equal volume of isopropyl alcohol. Instead of carboxylic acids at elevated temperatures, the 5-hydroxy 3-ketones may preferably be dehydrated with a mineral acid, preferably hydrochloric acid, at low temperatures between room temperature and $-20°$ C, preferably between $0°$ and $5°$ C. The normality of the mineral acid may range between 0.5–6 N, the preferred range being 1.0–4.0 N. The duration of this acid treatment may range from 2–100 hours, depending on the normality of the acid and the temperature.

The working up of the reaction mixture, containing the ketones, some residual starting material, possibly some α-bromo ketones, excess N-bromoacetamide and acetamide, may be effected by treatment with sodium thiosulfate, dilution with water, addition of an inorganic salt, such as sodium chloride to lower the solubility of the steroids in the aqueous phase and repeated extraction with a water-immiscible solvent, e.g. with chloroform. Preferably it may be effected by successive treatment of the reaction mixture with zinc powder; 30 grams per gram of starting material may be used, and 1–3 grams of sodium bicarbonate per gram of the N-bromoacetamide. Subsequent filtration, concentration with intermittent addition of water can then, e.g. in the case of the oxidation of digitoxigenin to digitoxigenone and the oxidation of digoxigenin to the corresponding 3-monoketone and 3,12-diketone, afford the ketonic products as precipitates. In the case of the formation of strophanthidone an aqueous solution is obtained, to which hydrochloric acid is added to effect the dehydration as outlined above; subsequent neutralization of the acidic mixture, for example with sodium bicarbonate, affords then the corresponding 4-en-3-one 5-anhydrostrophanthidone as a precipitate, which is readily collected by filtration.

Considering the preferred deoxygenation of the 3-oxo-14β-hydroxy cardenolides by zinc under the special conditions of the present invention, this may be brought about by treatment of the ketones, which are dissolved in a co-solvent, preferably methylene chloride, toluene or tetrahydrofuran, with zinc and a limited amount of a carboxylic acid, preferably 90% formic acid. The limited amounts of acid to be used are determined individually for each reaction. For the deoxygenation of saturated 3-ketones, 15–50 parts, and preferably 20–35 parts of 90% formic acid are used, while for the deoxygenation of 4-en-3-ones and 4,9(10)-dien-3-ones, 1–25 parts, preferably 5–15 parts are used in the case that the formic acid is added in one lot. The volume of co-solvents and the weight of zinc powder may range between 10–500 ml, preferably 50–150 ml, and 10 to 200 g, preferably 25–40 g, respectively. Good shaking or stirring is necessary during the deoxygenation and inert solid matter, such as glass beads may be added for a better dispersion of aggregates of zinc powder.

In the case of saturated 3-ketones additional hydroxy groups present in the molecule, such as 19- or 12-hydroxy groups, may be converted to their formates. It may also be difficult to deoxygenate the saturated 3-ketones completely without an increase in the formation of by-products or without retreatment of the product under the deoxygenation conditions. It is a special feature of the deoxygenation method that the deoxygenation of saturated ketones can be readily brought to completion before excessive formate and by product formation has taken place when the formic acid is added in small lots to the agitated reaction-mixture. Also less formic acid is then required for the deoxygenation which, moreover, can be completed in a shorter period of time. Thus for example in the case of the deoxygenation of 14β,19-dihydroxy-3-oxo-5β-cardenolide, the deoxygenation can be brought to completion within a day with only minor 19-formate formation, when 8 ml of 90% formic acid per gram of ketone are added in 8 lots during 160 minutes.

With regard to the separation of 5β- from 5α-isomers in the crude products, e.g., such as formed in the deoxygenation of 4-en-3-ones, the difference in the rf-values of the 5β- and 5α-isomers of 3-deoxy 19-alcohols 14β,19-dihydroxy5α-card20(22)-enolide and 3-deoxycannogenol is sufficient for an effective chromatographic separation. By contrast the rf-values of the 5β- and 5α-isomers of the corresponding 19-formates and acetates, as well as of the 10β-methyl and probably also of the 10β-hydrogen 3-deoxy analogs, are very similar and the separation of these isomers by chromatography is considerably more difficult. In the case of the above 19-alcohols the separation between the 5β- and 5α-isomers is even more readily accomplished, when they are converted to the corresponding 19-formates which then are subjected to hydrolysis conditions, e.g. to treatment with aqueous sodium bicarbonate in methanol. Under sufficiently mild conditions, essentially only the 5β-hydrogen 19-formates are hydrolyzed and the resulting mixture of 5β-hydrogen 19-alcohols and 5α-hydrogen 19-formates is readily separated by simple recrystallization or precipitation methods. The separation of the mixtures of 5β- and 5α-hydrogen 19-alcohols is less effective by the latter methods and it is preferable to take recourse to chromatographic separation. The 5β- and 5α-hydrogen isomers of 19-hydroxy steroids other than cardenolides can also be readily separated via intermediate 19-acylate formation and subsequent selective hydrolysis, e.g., the separation of 19-hydroxy-20β-pivaloxy-5β-pregn-8(14)-ene and the 5α-isomer can be readily effected via conversion to the 19-acetates and subsequent hydrolysis. 14β,19-Dihydroxy-5β-carda-3,20(22)-dienolide and 3-deoxycannogenol are readily converted to their 19-formates when the duration of the treatment of the corresponding ketones, used as starting materials, with zinc and formic acid is prolonged. Minor amounts of a by-product, considered to be the corresponding 14-anhydro analogs, are then also formed. The formylation can also be effected in absence of zinc by treatment of the 19-alcohols with 90% formic acid in a co-solvent, such as methylene chloride.

The processes of the 3-deoxygenation of aglycones may be illustrated by the conversion of strophanthidin to 3-deoxycannogenol and its 3-dehydro analog:

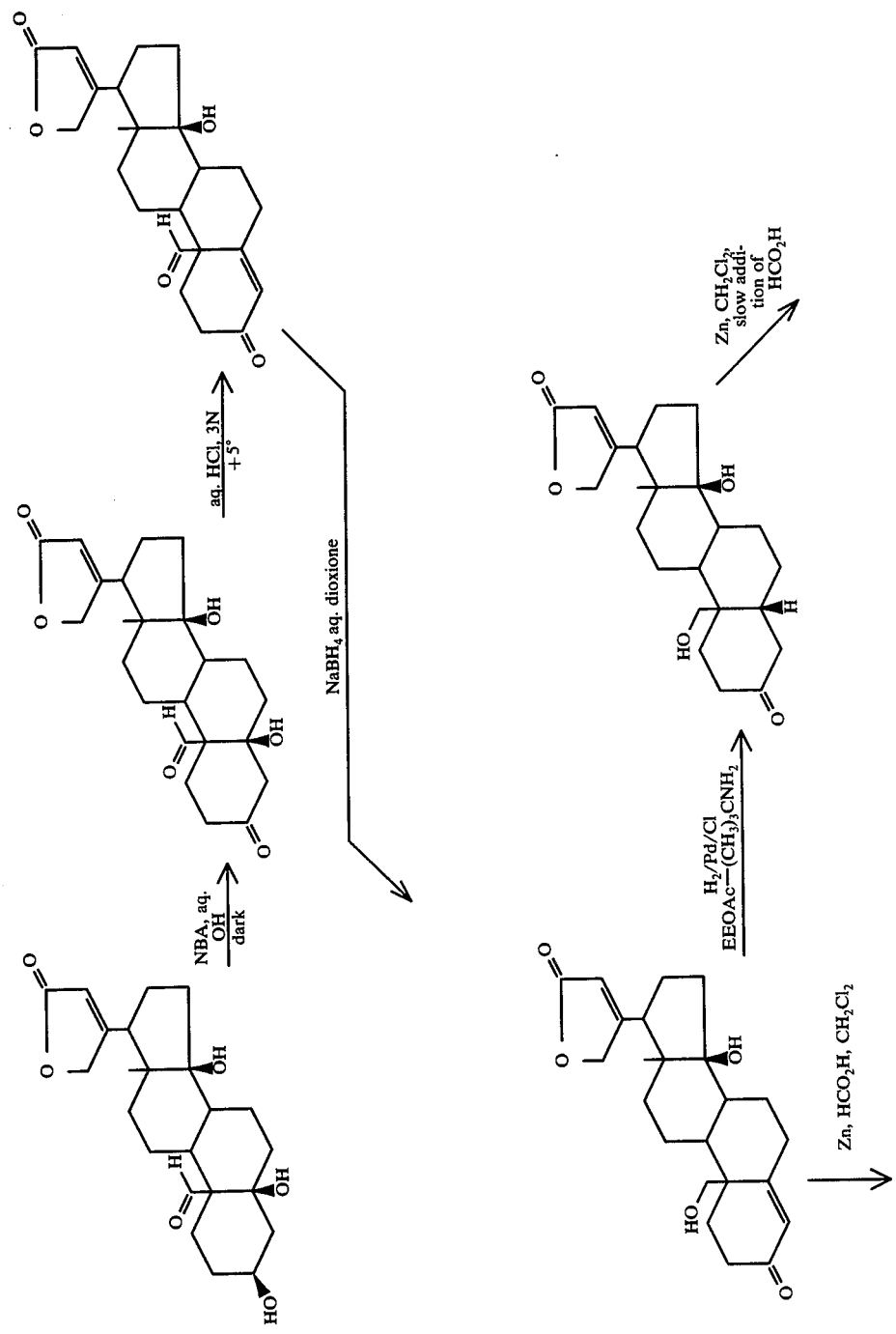

-continued
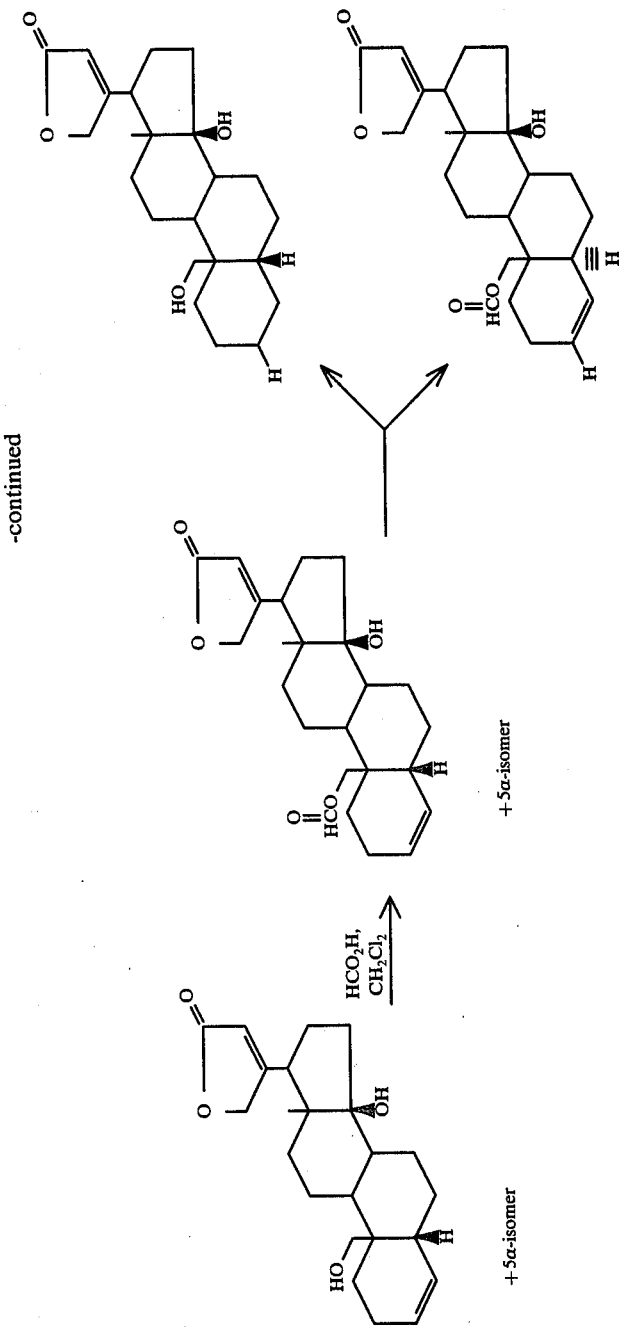

The conditions of the deoxygenation of 3-keto 14β-hydroxy cardenolides by zinc and limited amounts of carboxylic acid, in particular formic acid, can also be applied to the deoxygenation and reduction of other keto steroids and their oximes. In particular, it may be applied to the deoxygenation of saturated and conjugated 3-keto steroids which are not 14β-hydroxy cardenolides and to the reduction of 16-dehydro 20-keto steroids and their 20-oximes to 20α-alcohols and 20ε-amines respectively. For example 19-hydroxy- and 19-acetoxy-20β-pivaloxy-5β-pregn-8(14)-en-3-one, 19-hydroxy-20β-pivaloxypregna-4,7-dien-3-one, 19-hydroxy-20β-pivaloxypregna-4,6,8(14)-trien-3-one, prednisolone acetate, hydrocortisone alcohol, 5β-pregnane-3,20-dione, 5α-androstane-3,17-dione, progesterone, androst-4-ene-3,17-dione, stigmasta-4,20(22)-dienone, 16-dehydroprogesterone, 16-dehydroandrostenolone acetate and its oxime may be readily converted to deoxygenated or reduced products, respectively.

The conditions of the deoxygenation are also considered suitable for the introduction of tritium and deuterium into the 3,5 and 20-position using as starting materials the corresponding saturated and conjugated 3-ketones or 16-dehydro-20-ketones and tritiated or deuterated carboxylic acids.

Under the conditions applicable to the deoxygenation of saturated and conjugated 3-ketones, other unconjugated keto groups in the steroid molecule such as the 12-, 17- and 20-keto groups remain unaffected. Nonconjugated 3-ketones having a 5β-hydroxy group are reduced much less readily than 5β- and 5α-hydrogen 3-ketones. The butenolide ring, which remains unaffected, provided there is a hydrogen atom in the 22-position, is hydrogenolyzed at the 21-position to the corresponding α-carboxylated crotonic ester, if there is a $CO_2$alkyl, e.g. a $CO_2CH_2C_6H_5$ group, in the 22-position (see West German published application P 24 55 272.5). If, in the deoxygenation of 4-en-3-ones, there is a hydroxy or acyloxy group present in the 21- or 17α-position of a 20-ketone, i.e. in the α-position of the latter, this may remain unaffected, as does a double bond in the homoconjugated 7-position. In the case of 19-aldehyde 3,19-dioxo-14-hydroxy-14β-carda-4,20(22)-dienolide two not yet identified major compounds appear to be formed instead of the less polar analogous 3-deoxy 3-enes.

The same products are formed when the 5,19-hydrogen peroxide adduct of 3,19-dioxo-14-hydroxy-14β-carda-4,20(22)-dienolide (see below), is subjected to treatment with zinc and formic acid. Irradiation of the peroxide adduct gives an unknown acid, which under the deoxygenation conditions using zinc gives the corresponding 3-dehydro 19-carboxylic acid. Treatment with diazomethane of the latter gives the 19-methyl ester which was found to be identical with the ester obtained by deoxygenation and subsequent esterification of a mixture of 19-carboxy-5,14-dihydroxy-3-oxo-5β,14β-card-20(22)-enolide and the corresponding 4-en-3-one.

In the case of 4,6-dien-3-ones, only small amounts of the formally expected 3,6-dienes appear to be formed. In the case of 4,9(10)-dien-3-ones the proportion of the expected 3,9(10)-dienes appears somewhat larger. In the case of 4,6,8(14)-trien-3-ones, the 3-deoxy steroids obtained may be the corresponding 5,7-cyclo-3,8(14)-dienes. 16-Dehydro-20-ketones give 20α-hydroxy-16-enes rather than 20-deoxy analogs.

In the reduction of the 16-dehydro-20-ketones even less formic acid is required than for the deoxygenation of 4-en-3-ones under identical conditions. The formation of 20α-hydroxy-16-enes from the conjugated 20-ketones can also be effected by a minimal amount of acetic acid, e.g., as little as 10 parts in 75–150 parts of methylene chloride or toluene being sufficient.

Considering in detail the conversion of 3-ketones to the 3-deoxy 14β-hydroxy cardenolides via their tosylhydrazones this may be effected by treating the ketone with 1 part of tosylhydrazine at room temperature for 90 minutes, followed by evaporation and treatment of the thus formed tosylhydrazone with 2 parts of sodium borohydride in 50 parts of methanol first at 0° C and then at room temperature for 1.5 hours. Quenching with acetone and 0.1 N aqueous hydrochloric acid gives after neutralisation with sodium bicarbonate, a product consisting of the deoxygenated ketone and the corresponding 3-alcohols.

The aglycones used in the oxidation to the 3-ketones may be obtained from the corresponding glycosides found in nature. For example strophanthidin is the aglycone of the three glycosides comprising strophanthin k, one source of which is the seeds of the plant *Strophanthus kombe*. The commercial product also contains glycosides of the corresponding 19-alcohol, i.e. of *strophenthidol*, which can be converted to 14β,19-dihydroxy-3-oxo-carda-4,20(22)-dienolide, a key intermediate in the preparation of the valuable 3-deoxycannogenol. Strophanthin *k* is the cheapest among the cardenolides isolated from natural sources. Also commercially available and relatively cheap are the glycosides digitoxin, the 12-hydroxylated glycoside, digoxin and the 1β,5β,11α-hydroxylated glycoside ouabain, which on hydrolysis afford digitoxigenin, digoxigenin and ouabagenin, respectively, and occur in the plants Digitalis purpurea, Digitalis lanata and Strophanthus gratus (see "The Merck Index").

In the case of the oxidation of ouabegenin and subsequent dehydration of the resulting 1,5-dihydroxy 3-ketone to the corresponding 1,4-dien-3-one it would be necessary to protect the 19-hydroxy group, e.g. by a formyl or acetyl group, to prevent aromatization to the corresponding phenolic 1,3,5(10)-trien-3-ol.

Among the more common aglycones obtainable from naturally occurring glycosides which are not commercially available are sarmentogenin, sarmutogenin, caudogenin and sinogenin. The compounds are 11α-hydroxy, 11-keto 12β-hydroxy, 11-keto 12α-hydroxy and 11α-hydroxy 12 keto analogs respectively, of digitoxigenin; the latter 3 compounds can all be oxidized to the corresponding 3,11,12-triketone sarmutogenin (see Fieser and Fieser, "Steroids," cited above, pp. 774, 775; see also "The Merck Index," 7th Edition, 1960, p.921).

Similarly sarmentogenin may be oxidized to the corresponding 3,11-diketone and the method of this invention used for the oxidation of the 3β,12β,14β-trihydroxy triol digoxigenin to the corresponding 3,12-diketone by N-bromoacetamide may be employed. Also the 5α-cardenolide panogenin, i.e. 11β,14,19-trihydroxy-5α,14β-cardenolide, which occurs in nature in the form of panoside, a highly potent glycoside, may give a 3-keto 14β-hydroxy cardenolide with an oxygen function in the C-ring.

The 3-ketones and their 4-dehydro analogs obtained by the oxidation of the aglycones may be further converted to other 3-oxo-14β-hydroxy cardenolides. Thus strophanthidone obtained from strophanthidin can be, according to a procedure of this invention, converted to the corresponding 19-carboxylic acid by exposure to daylight as described above. The carboxylic acid can then be converted, for example, and again according to a procedure of this invention, by heating of the filtrate after the zinc treatment, to the corresponding 5(10)-en-3-one. The latter homoconjugated ketone can give the corresponding conjugated 19-nor-4-en-3-one by acid or base catalyzed rearrangement or by prolonged heating and can also be converted to the corresponding 4,9(10)-dien-3-one by treatment with pyridinium hydrobromide perbromide according to a modified literature procedure used in the preparation of 9(10)-dehydro analogs of hormonal steroids (M. Perelman, E. Farkas, E. J. Fornefeld, R. J. Kraay and R. T. Rapala, J. Am. Chem. Soc., 82, 2402 (1960)). The 19-nor-4-en-3-one analog of strophanthidone, i.e. 3-oxo-14β-hydroxycarda-4,20(22)-dienolide can also be obtained by treatment of the corresponding 19-aldehyde, i.e. 3,19-dioxo-14β-hydroxycarda-4,20(22)-dienone, with methanolic potassium hydroxide preferably by a modification of the procedure of S. M. Kupchan, C. J. Sih, N. Katsui, O. El. Tayeb, J. Am. Chem. Soc., 84, 1753 (1962). The latter 3,19-dioxo cardenolide, on selective reduction by sodium borohydride in aqueous dioxane or by lithium borohydride in pyridin employing special methods of this invention affords 14β,19-dihydroxycarda-4,20(22)-dienolide, which is a valuable intermediate for the preparation of 3-deoxycannogenol. Selective hydrogenation of the 19-hydroxy-4-en-3-one with palladium on charcoal as the catalyst in ethyl acetate in presence of tertiary butylamine (see also G. Kruger, Steele Chemicals, U.S. Pat. No. 3,647,829 and Canadian Patent 881,604) affords 3-oxo 14,19-dihydroxy-5β,14β-cardenolide with only very little attending formation of the 5α-isomer.

The aldehyde 3,19-dioxy-14-hydroxy-14β-carda-4,20(22)-dienolide, the corresponding 19-oic acid and the homoconjugated ketone 3-oxo-14-hydroxy-19-nor-14β-carda-5(10),20(22)-dienolide can also be converted to 10β-hydroperoxy-3-oxo-19-norcarda-4,20(22)-dienolide by oxidation with molecular oxygen. The corresponding 10β-hydroxy analogs are readily obtained by reduction of the 10β-hydroperoxides with sodium iodide. Employing hydroperoxide and special conditions the above 19-aldehyde can be converted into an adduct considered to be formed by initial addition of hydrogen peroxide to the 19-aldehyde group and to possess a 5,19-peroxide bridge. Oxidation of 5β-hydroxy 19-aldehyde strophanthidone to the corresponding carboxylic acid can be accomplished by oxidation with molecular oxygen as well as by treatment with hydrogen peroxide, in light.

Similarly the 14β-hydroxy-3-oxo-carda-4,9(10),20(22)-trienolide may be converted into its 3,5(10),9(11)-trien-3-ol, the corresponding 3-acetate or 5(10),9(11)-dien-3-one, which then on oxidation with molecular oxygen may give the corresponding (J. J. Brown and S. Bernstein, Steroids, 8, 87 (1966)) 11β-hydroperoxy-4,9(10)-dien-3-one and hence the corresponding 11-alcohol by reduction. The 14β-hydroxy 4,9(10)-dien-3-one obtained from the 5(10)-en-3-one, may also be dehydrated to the corresponding 4,9(10),8(14)-triene, which on treatment with a cis-hydroxylation agent, possible after saturation of the double bonds in the 4- and 9(10)-position of the conjugated trienone, could give the corresponding 8β,14β-diol.

The 3-deoxy cardenolides formed by selective deoxygenation of the 3-keto 14β-hydroxy cardenolides may be further converted to other 3-deoxy compounds of this invention. Thus their hydroxy groups may be acylated or converted to the corresponding tetrahydropyranyl ethers.

Also the butenolide ring may be hydrogenated to yield the corresponding cardanolides. Isomeric 20-R or 20-S cardanolides may be obtained predominantly depending on the conditions of the hydrogenation, e.g whether it is being carried out with palladium on charcoal in methanol, with platinum in the same solvent, or with palladium on charcoal in presence of t-butylamine. In the case the latter conditions are employed the butenolide ring can be hydrogenated preferentially, before the isolated double bond in position 3, present in some of the compounds of this invention.

Further the deoxy 14β-cardenolides having additional double bonds may be selectively hydrogenated, β-epoxidized or β-hydroxylated to form the corresponding dihydro analogs, e.g. 3-deoxycannogenol from 3(4)-anhydrocannogenol, 5β,10β-and 9β,10β-oxido and 5β,10β- and 9β,10β-dihydroxy analogs from 14β-hydroxy-19-norcarda-5(10),20(22)-dienolide or 14β-hydroxy-19-norcarda-9(10),20(22)-dienolide, respectively, employing typical methods and reagents used commonly for such conversions.

It is also within the scope of the modifications to convert the 3-deoxy 14β-hydroxy cardenolides having additional double bonds to the corresponding seco cardenolides by selective ozonolyses and to deoxygenate the resulting aldehyde or keto groups at the site of fission of the olefinic bonds to the corresponding alkyl groups; 2,3-, 5(10)- and 9(10)-seco 14β-hydroxy cardenolides may thus be obtained.

The 3-deoxy 14β-hydroxy cardenolides having keto groups in the C-ring may be converted to α-substituted analogs, e.g. the 3-deoxy 12-oxo-digitoxigenin obtained from digoxigenin may be converted to the 11-hydroxy 12-keto analog. 3-Deoxy 14β-hydroxy cardenolides having an 11α-hydroxy group may be oxidized selectively to the corresponding 11-ketones, e.g. by the method of this invention employing N-bromoacetamide, and may then be reduced, e.g. by sodium borohydride, to the corresponding 11β-hydroxy analogs.

Hydroxy groups may also be introduced into the 7, 8, 9, 11, 12 and 19-position of 3-deoxy 14β-hydroxy cardenolides by microbiological reactions (see for example, L. L. Smith in "A Specialist Periodical Report, Terpenoids and Steroids," The Chemical Society, London, 1974, pp 394–530; for the 12β-hydroxylation of digitoxigenin see A. Gubler and Ch. Tamm. Helvitica Chim. Acta, 41, 297 (1958)), and by enzymatic preparations (for the hydroxylation of a steroid by sow ovarian 19-hydroxylase see M. P. Kautsky, G. W. Thurman and D. D. Hagerman, J. of Chromatography, 114, 473 (1975)).

The 3-deoxy steroids, which do not belong to the class of cardenolides and have been obtained by the deoxygenation of the corresponding 3-ketones with the help of the preferred deoxygenation methods of this invention, may be further modified to yield other deoxy steroids. Thus 19-acetoxy-20β-pivaloxy-5β-pregn-8(14)-ene, which has been obtained by deoxygenation with zinc and formic acid and also by the method, in which the ketone is first converted to the tosylhydrazone, has been converted to deoxycannogenol 19-formate via a series of 3-deoxy intermediates (see G. Kruger, Can. J. Chem., 52, 4139 (1974)), where the conversion of a 3-oxygenated 19-hydroxy-8(14)-ene of the 5α-series to 14β-hydroxy-5α-cardenolides by a similar route has been described.

The above 3-deoxy 8(14)-ene has also been converted to 14β-hydroxy-20β-pivaloxy-5β-cardenolide 19,8-lactone by conversion into the 19-hydroxy-8β,14β-oxide and subsequent oxidation. The above 3-deoxy 8(14)-ene has further been converted to the corresponding 19-tetrahydropyranyl ether, thence to the corresponding 20β-alcohol and 20-ketone which on hydrolysis of the tetrahydropyranyl ether group gave 19-hydroxy-5β-pregn-8(14)-en-20-one. This compound, after conversion to the 19-acetate, could give the 21-acetoxy analog on oxidation with lead tetraacetate, as indicated by the analogous oxidation of a 3β-acetoxy-8(14)-en-20-one of the 5α-series. Further reactions could then afford the corresponding 19-acetoxy carda-8(14),20(22)-dienolide (see for example G. Kruger, Can. J. Chem., 52, 4139 (1974)).

Regeneration of the 19-hydroxy group of the latter compound and epoxidation could give the corresponding 3-deoxy-8β,14β-oxide which by acid treatment or oxidation to the corresponding 19-carboxylic acid or 19-aldehyde and subsequent or concommitant acid treatment could then give the 3-deoxy 14β-hydroxy cardenolides, 14-hydroxy-8,19-oxido-5β,14β-card-20(22)-enolide (see co-pending Canadian Application Serial No. 131,672) or 14-hydroxy-5β,14β-card-20(22)-enolide 19,8-lactone (see co-pending Canadian Application Serial No. 131,674) and the corresponding 19,8-lactol respectively. Similarly, the deoxygenation product of 19-hydroxy-4,6,8(14)-trien-3-one, which is considered to be a 5,7-cyclo-19-hydroxy-3,8(14)-diene may be converted to the corresponding 5,7-cyclo 3-deoxy 14β-hydroxy cardenolides employing the methods used previously for the conversions of other 19-hydroxy-8(14)-enes. The initial step would involve the selective hydrogenation of the double bond in position 3.

The 19-hydroxy-20β-pivaloxy-5β- and 5α-pregna-3,7-diene, which have been obtained by the deoxygenation of the corresponding 4,7-dien-3-one, may be converted to the analog with a saturated A-ring by selective hydrogenation of the double bond in position 3. Further subjection to the hydrogenation condition would be expected to convert the 7-ene or the 5α-series to the 5α-isomer of the above discussed 3-deoxy-8(14)-ene. The 7-ene of the 5β-series may be converted to 14β-functionalized pregnanes and hence to 14β-hydroxy cardenolides by conversion to a 20β-hydroxy-7-ene and application of recently developed methods by which 22-hydroxy-7-enes are converted to 14β-hydroxy analog via their 14,22-oxides (see E. Caspi, D. J. Aberhort, Ger. Offenlegungsschrift 2, 162, 224; E. Caspi and D. J. Aberhart, J. Chem. Soc. (C), 1971 2069). The 7-ene may also be converted to the 7,8-seco 7,8-dioxo analog, in which 14β-hydroxylation, i.e. adjacent to the 8-oxo group, may readily be accomplished.

The 3-deoxy 14α-hydrogen steroids accessible by the deoxygenation method, especially the 11β-and 19-hydroxy-21-acetoxy-20-ones of the 14α-pregnane series and 19-hydroxy steroids of the 14α-cardenolide series (see for example co-pending Canadian Application Ser. No. 186,960, Experiment 6; the preparation of 19-acetoxy-3-oxocarda-4,6,20(22)-trienolide is described, which could be hydrogenated to the corresponding 4-en-3-one or 5β-hydrogen 3-ketone and thence could afford the 3-deoxy 14α-hydrogen cardenolides) could be converted to 15α-hydroxy or 14α-hydroxy analogs (see for example, G. D. Meakins, J. W. Blunt, L. M. Clark. J. M. Evans, E. R. H. Jones, J. T. Pinhey, J. Chem. Soc. (C), 1971, 1136)which then could afford the corresponding 3-deoxy 14β-hydroxy cardenolides via dehydration to the respective 14-enes (see for example, W. Fritsch, V. Stache, W. Haede, K. Radscheit and H. Ruschig, Liebigs Ann. Chem., 721, 168 (1969)).

Table 1 summarizes the major biological activities which were assessed for the 3-deoxy 14β-hydroxy cardenolides and digoxin, which is presently the most widely used cardiotonic agent.

The inotropic effects have been determined with spontaneously beating atrial preparations derived from guinea pigs. The ATP-ase was obtained from the brain of the same animal and the methods of Okita et al (1973) and of Kupchan et al (1964) were employed. The lethal dose in cats was determined by the method of Chen.

A comparison of the inotropic effect and lethal dose of 3-deoxycannogenol and digoxin reveals that, on a molar basis, 3-deoxycannogenol is about 2–4 times more inotropic and less than half as toxic as digoxin. A comparison of the ATP-ase inhibition of the two compounds indicates that digoxin could be more than 3 times as toxic as 3-deoxycannogenol as ATP-ase inhibition has been considered as a measure of toxicity. That the latter compound is less toxic than digoxin is also indicated by the appearance of arrhythmia, when digoxin is administered in doses greater than those causing an increase in contractile force of 60%, while with 3-deoxycannogenol no arrhythmia were observed at doses causing an increase of 90% of contractile force. 3-Deoxycannogenol showed no emetic effects in cats at intravenous doses amounting to 1/10 and 1/100 of the lethal dose.

The inotropic effect and ATP-ase. inhibition of 14,19-dihydroxy-5β,14β-carda-3,20(22)-dienolide are, as the table shows, generally between those of 3-deoxycannogenol and digoxin. In the inotropic tests 14,19-dihydroxy-5β,14β-carda-3,20(22)-dienolide was found similar to 3-deoxycannogenol, to be considerably less arrhythomogenic than digoxin.

In the inotropic tests it was observed that the number of washings to remove the tested compounds from the bath decreased in the following order of compounds: digitoxin > digoxin > 3-deoxycannogenol > 14,19-dihydroxy-5β,14β-carda-3,20(22)-dienolide > strophanthidin 3-acetate.

TABLE I

Inotropic activity, lethal doses and ATP-ase inhibition of 3-deoxycannogenol, 14,19-dihydroxy-5β,14β-carda-3,20(22)-dienolide and digoxin

| Compound | Molar concentration causing increase in contractility | | | Lethal Dose for cats | | Molar concentration causing 50% ATP-ase inhibition |
| --- | --- | --- | --- | --- | --- | --- |
| | 30% | 50% | 80% | mg/kg | micromoles/kg | |
| (structure 1) | $7.2\times10^{-7}$ | $1.1\times10^{-6}$ | $1.95\times10^{-6}$ | 0.459 | 1.23 | $8.3\times10^{-6}$ |
| (structure 2) | $2.2\times10^{-6}$ | $2.8\times10^{-6}$ | $4.0\times10^{-6}$ | — | — | $6.2\times10^{-6}$ |
| digoxin | $1.4\times10^{-6}$ | $2.8\times10^{-6}$ | $8.0\times10^{-6}$ | 0.354 | 0.453 | $2.67\times10^{-6}$ |

Table 2

Preliminary biological tests on 3-deoxy 14β-hydroxy cardenolides

| Compounds | Molar concentration causing | | ATP-ase inhibition | |
| --- | --- | --- | --- | --- |
| | 30% | 50% | % inhibition at a $1\times10^{-4}$ molar concentration | % reversibility of inhibition |
| | increase in contractility | | | |
| (structure) | $2.9\times10^{-6}$ | — | — | — |

Table 2-continued
Preliminary biological tests on 3-deoxy 14β-hydroxy cardenolides

| Compounds | Molar concentration causing 30% increase in contractility | Molar concentration causing 50% increase in contractility | ATP-ase inhibition % inhibition at a 1×10⁻⁴ molar concentration | ATP-ase inhibition % reversibility of inhibition |
|---|---|---|---|---|
| [structure: HCO-O, OH, H, H] | — | — | 41 | 84 |
| [structure: HO, OH, H, H] | $1.85 \times 10^{-5}$ | $4 \times 10^{-5}$ | 45 | 57 |
| [structure: FmO, OH, H, H] | $5.0 \times 10^{-5}$ | — | 42 | 95 |
| [structure: H, OH, H, H] | — | — | 59 | 76 |
| [structure: HO, OH, H, H] | inactive | — | 63 | 81 |

The 3-deoxy 14β-hydroxy cardenolides of the present invention, having additional oxygen functions at position 19 and in the B- and C-ring and the 3-deoxy 14β-hydroxy 19-nor cardenolides represent novel classes of compounds; an additional feature of various of these compounds is the presence of double bonds in A and and at the C-ring. In the preparation of some of the 3-deoxy 14β-hydroxy cardenolides, the 3-keto precursors are themselves novel compounds; e.g. 14-hydroxy-3-oxo-19-norcarda-5(10),20(22)-dienolide, 14-hydroxy-3-oxo-4,9(10) and -5-(10)9(11)-dienolide and 3-oxo,14,19-dihydroxy5β-card-20(22)-enolide appear to be novel ketones.

The compounds of the present invention are useful as cardiotonic agents as they possess the structural elements necessary for cardiotonic activity. Thus, they possess the 14β-hydroxy group and the 17β-butenolide ring which is present in the prominent cardiotonic steroids used currently in medicine, e.g. in digoxin, digitoxin and strophanthin k. All 14β-hydroxy cardenolides, which have been used in medicine, have been isolated from natural sources or have been obtained by minor chemical modification of compounds obtained from the latter and contain a glycosyloxy group or another oxygen function in the 3-position. The compounds of the present invention are especially useful since they are not encumbered by glycosyloxy groups other oxygen functions in the 3-position such as present not only in the medicinally used 14β-hydroxy cardenolides but apparently also in all naturally occurring heart-active steroids.

There are several reasons why it is believed that the removal of the oxygen function at position 3 can lead to a cardiotonic agent of improved therapeutic utility.

One reason is that generally it is better to remove all groups containing oxygen, nitrogen and other hetero atoms, which do not contribute to the desired activity, since these groups in contrast to hydrocarbon moieties, which may be considered to be generally void of physiological activity can be themselves sites of other, undesired physiological activites. This simplification of the active molecule may be compared to the separation of the active principle from associated matter not contributing to the desired physiological activity of drugs and has in the past led to major improvements of the latter.

Also, the structurally simplified molecules lend themselves as reference compounds for the establishment of improved structure-activity relationships and thence can be of aid in the design of compounds, which could be even simpler or could contain selected additional activity promoting groups with improved therapeutic action.

Further, structurally simplified molecules have the advantage that their metabolic fate can be more readily assessed by the available analytical methods and hence their administration to the patient can be better regulated. Yet further, they have the advantage of being generally more readily obtainable by total synthesis from basic chemicals and hence could become less expensive.

The conversion of the glycosyloxy group into the corresponding 3β-hydroxy group by hydrolysis will conceivably be considered as an already adequate and useful simplification. The activity of the aglycones thus obtained is, however, less than that of the corresponding glycosides and according to recent findings this is due to the enzymatic epimerization of the aglycones to the 3α-epimers, which are devoid of activity. One function of the glycosyl group appears then to protect the 3β-hydroxy group from epimerization, and considering further that some metabolic degradation of the glycosyloxy group does take place after administration, and that the 3-oxygen function is not indispensible for heart activity, it appears (see also Y. Saito, Y. Kanemasa and M. Okada, Chem. Pharm. Bull., 18, 629 (1970); K. Takeda, T. Shigei and S. Imai, Experientia, 26, 867 (1970); T. R. Witty, W. A. Remers and H. R. Besch, J. Pharmaceut. Sci., 64, 1248 (1975)) useful to eliminate the 3-oxygen function altogether rather than to attempt the preparation of analogs with improved activity by its chemical modification, as has been frequently done before.

Among the different individual compounds of this invention, 3-deoxycannogenol (19-hydroxy-3-deoxydigitoxigenin) was found to possess so far the greatest utility as a superior cardiotonic agent.

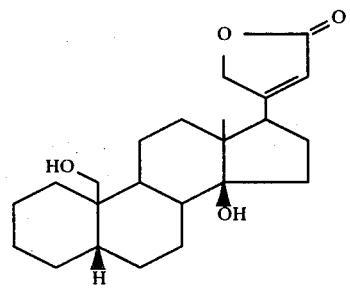

Thus, in biological tests (see Table 1 and description of biological effects) it has been shown to promote the contraction of heart muscles considerably more strongly than digoxin, the cardiotonic agent presently most widely used in medicine. Yet, its toxicity is substantially lower than that of digoxin. 3-Deoxycannogenol thus shows a greater dissociation between beneficial and toxic activity i.e. it is not only more active but also has a better therapeutic index. All natural cardiotonic steroids are known for their low margin of safety due to an uncomfortably close association between cardiotonic activity and toxicity and the opinion that the ratios between the latter do not differ essentially between the individual compounds has frequently been stated or implicated, however, because of their life-saving potential their toxicity has been accepted in medicine. 3-Deoxycannogenol thus has the potential of a life-saving cardiotonic drug with a lower than hitherto known and considered achievable, relative toxicity.

A further usefulness of 3-deoxycannogenol resides in the fact that it is considerably more lipohilic than the 19-oxygenated cardenolides obtained from natural sources or by minor chemical modification of these. Although the latter, typical members of which are ouabain, strophanthin k and strophanthidin 3-acetate, are valued in medicine and biological research for their high intravenous activity, fast onset and short duration of activity, they show only a rather low oral activity. As the increase in lipophilicity is generally accompanied by an increase in oral activity, 3-deoxycannogenol would be expected to be considerably better absorbed than the more polar 19-oxygenated cardenolides obtained from natural sources.

The duration of activity is similarly dependent on lipophilicity, the more polar compounds being more readily eliminated. The observation that in the inotropic tests 3-deoxycannogenol is more readily removed from the bath, containing the heart muscle, by repeated washing, than digoxin and less readily than the more polar strophanthidin 3-acetate suggests that its duration of activity could be between the two latter compounds and is considerably shorter than that of digitoxin, i.e., it is in a desirable range.

Also, usefulness of 3-deoxycannogenol resides in that its distribution within the human body and its metabolic transformation should be, because of its simpler structure and the presence of the primary 19-hydroxy group which lends itself for suitable derivatization, be considerably easier assessed than that of cardenolides presently used in heart-therapy. The latter are all oligoglycosides and tend to be metabolized to the corresponding lower glycosides and to the genins which themselves tend to be metabolized to the 3α-hydroxy epimers. The 19-alcohol 3-deoxycannogenol would be expected to afford readily a polyfluorinated 19-acylate, such as the 19-heptafluorobutyrate, which is detectable in pico gram quantities by electron capture, e.g. in gas chromatography. (for the analysis of digoxin and digitoxin by gas chromatography see E. Watson, P. Tramel and S. M. Kalman, J. of Chromatography, 69, 157 (1972), E. Watson and S. M. Kalman, J. of Chromatography, 56, 209 (1971); see also M. C. Castle, J. of Chromatography, 115, 437 (1975) and Chem. & Eng. News, March 22, 1976, p.32.) The cardenolides presently used in heart therapy lend themselves considerably less readily to gas-chromatographic determination, which is valued for its relatively high accuracy and versatility, as in their derivatization they have to be converted to the genins and also require separation from the resulting sugars. Because of the narrow margin of safety of cardiotonic steroids, the determination of their uptake by the patient, in particular the determination of the plasma concentrations of the latter, plays an important role in heart-therapy.

With respect to dehydro, 19-nor and 20(22)-dihydro analogs and of derivatives of 3-deoxycannogenol, the 3(4)dehydro analog of 3-deoxycannogenol, i.e. 3(4)-anhydrocannogenol has a greater inotropic activity than digoxin, though it is less active than 3-deoxycannogenol and also appears to be less toxic than digoxin. The 19-formate of 3-deoxycannogenol similarly has a substantial inotropic activity which equals about that of digoxin. The 19-nor analog

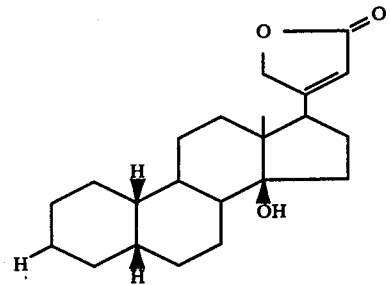

and the 20(22)-dihydro analog

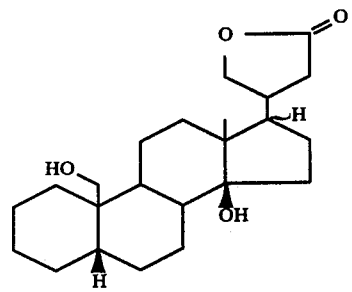

have been found to possess substantial heart-activities.

The 3-dehydro analog of 3-deoxycannogenol finds a special utility in that it is an intermediate in an important process of preparing 3-deoxycannogenol and that it allows the preparation of labelled 3-deoxycannogenin by selective tritiation of the olefinic double bond in position 3 and 4. The tritium atoms thus introduced would be in a non-exchangeable position and hence the tritiated 3-deoxycannogenol is useful for the monitoring of the metabolic fate of 3-deoxycannogenol, for example by the radioimmunoassay.

3(4)-Anhydrocannogenol may also be employed in the generation of the 3-deoxycannogenol specific antiserum required for the determination of 3-deoxycannogenol in the plasma of patients by the radioimmunoassay, as suitable antigenic proteins or other antigenic macromolecules may be attached to the 3- or 4-position by functions, such as 3,4-epoxides or 3,4-seco 3,4-dialdehydes, derived from the double bond in the 3-position.

The 3,4-dehydro analog of 3-deoxycannogenol may further be useful, for the conversion to the saturated 3,4-seco analog

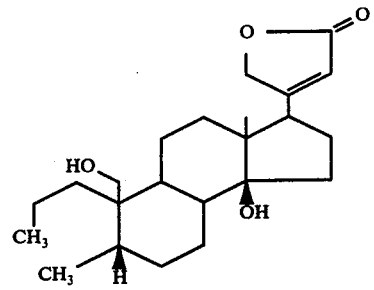

of 3-deoxycannogenol. This can be accomplished by selective ozonolysis, followed by deoxygenation of the resulting ozonide. The deoxygenated seco analog may be considered to be structurally even more simple than 3-deoxycannogenol, since it contains one ring less. In the case the 3,4-seco analog shows a useful physiological activity, also the synthesis of analogs of 3-deoxycannogenol not having the carbon atoms of the A-ring becomes indicated and could afford compounds having a simpler structure and still retain the useful physiological activity. That an intact A-ring is not indispensible for heart-activity has been shown in a recent publication (H. Tsuru, N. Ishikawa, T. Shigei, T. Anjyo and M. Okada, Experientia, 31, 955 (1975)). Similar to the 3-dehydro analog of 3-deoxycannogenol also the other olefins of formula I having a double bond in the 3-position, as for example 3-dehydro-3-deoxy-19-nordigitoxigenin, and also the olefins having isolated double bonds in other positions, may be used for the formation of seco 14β-hydroxy cardenolides; e.g. 5(10)-seco and 9(10)-dehydro-3-deoxy 19-nordigitoxigenin may give 5(10)-seco and 9(10)-seco 14β-cardenolides. The latter compounds may lead to the preparation of even more simple analogs which still could possess useful biological utility. In these analogs only the C and D-ring of the steroidal ring system would be retained and their total synthesis could be a relatively easy task.

The 19-formate ester of 3-deoxycannogenol, though being less active than 3-deoxycannogenol, may be useful as a "prodrug". As it is more lipophilic it may be even more readily absorbed orally than 3-deoxycannogenol, which after absorption of the formate ester may then be released by enzymatic hydrolysis. Also the duration of the activity may be favourably prolonged if 3-deoxycannogenol is administered as the formate. Similarly the other esters of 3-deoxycannogenol of formula I may be useful as effective prodrugs.

The utility of the 19-nor analog of 3-deoxycannogenol lies in the fact that it is the most simple 14β-hydroxy cardenolide with an intact steroid ring system which so far has been prepared. Therefore it is well suited as a reference compound for the development of improved structure activity relationships and hence is expected to be a useful tool in the design of improved cardiotonic compounds. Also containing only functions necessary for cardiotonic activity it may be relatively free of other undesired physiological activities.

The utility of the 20(22)-dihydro cardenolides, i.e., of the cardanolides of formula I lies in the observation that the dihydro analogs of cardenolides, though having a reduced inotropic effect, exhibit an even more reduced toxicity and hence have a better therapeutic ratio than the unsaturated analogs (see for example R. L. Vick, J. B. Kahn and G. H. Acheson, J. Pharmacol. Exp. Ther., 121, 330–339 (1957); see also R. F. Mendez, G. Pastelin and E. Kabela, J. Pharmacol. Exp. Ther., 188, 188–197 (1974)). The structure of the cardanolides may also be considered to be more simple than that of their cardenolide analogs.

With respect to 3-deoxy 14β-hydroxy cardenolides having additional oxygen functions in other than the 19-position, the utility of the additional hydroxy group in the 5β, 6β, 7β, 8β, 9β, 10β, 11β and 12β-hydroxy 3-deoxy cardenolides of formula I is considered to lie in their ability to increase heart-activity. As evident from emerging structure activity relationships, and as has long been recognized for the 19-hydroxy group, polar groups, in particular, hydroxy groups, on the β-side of the steroid molecule enhance, while those on the α-side, e.g. 3α-hydroxy groups, such as formed by enzymatic epimerization of 3β-hydroxy groups, reduce heart-activity.

That 8β-hydroxy groups enhance activity is in agreement with the high cardiac activity of scillirosidin

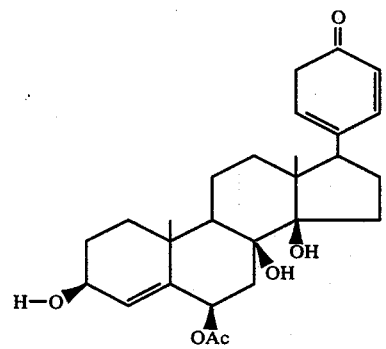

(see Fieser and Fieser,
"Steroids", cited above,
p. 808).

That 11β-hydroxy groups enhance cardiac activity is in agreement with the fact that panoside possesses a high cardiac activity,

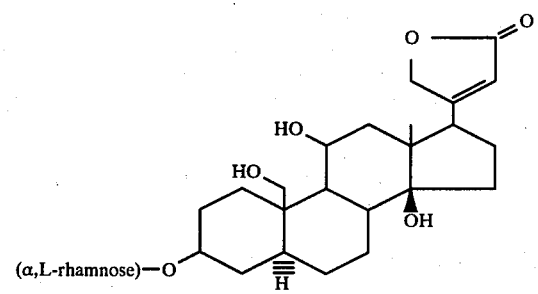

despite the presence of an activity reducing A,B-trans ring junction (see K. K. Chen., J. Med. Chem., 13, 1029 (1970)).

That 12β-hydroxy groups increase activity is indicated by a comparison of the activities of derivatives of digitoxigenin and its 12β-hydroxy analog digoxigenia (see Fieser and Fieser, cited above, p. 804). A 12β-hydroxy group is further useful since 12β-hydroxylation occurs under physiological conditions and hence it becomes unnecessary to contend with the metabolic transformation to 12β-hydroxy analogs in the monitoring of the digitalis levels of patients (see C. S. Davies and R. P. Halliday, "Medicinal Chemistry," edited by A. Burger, Wiley Interscience, New York, Part II, p. 1077).

That 5β-hydroxy groups enhance activity is in agreement with the observation that the cymaroside of 5β-hydroxydigitoxigenin is nearly twice as active as the cymaroside of digitoxigenin (see Fieser and Fieser, "Steroids", cited above, p. 802).

With respect to the processes used for the preparation of 3-deoxy 14β-hydroxy cardenolides from 3-oxo cardenolide analogs by deoxygenation with zinc and a carboxylic acid or by hydride reduction of the corresponding tosylhydrazones, no teachings are present in the prior art processes of preparing 3-deoxy 14β-hydroxy cardenolides. The process employing zinc and a carboxylic acid for the deoxygenation of a saturated 3-keto steroid, and possibly also for the deoxygenation of cyclohexanone moieties present in other nonsteroidal compounds, is not taught in the literature. It will be noted that in the deoxygenation of 4-dehydro-3-keto steroids by the latter process, predominantly 3-enes of the 5β-series, rather than of the 5α-series, are formed, in contrast to the literature procedures using zinc and acetic acid. It will further be noted that the novel procedures allow the deoxygenation of homoconjugated ketones, such as 5(10)-en-3-ones and 4,7-dien-3-ones without rearrangement of the labile homoconjugated double bond. Similarly the scope has been extended to include 4-dehydro-3-ketones, which are 19-nor steroids. In the case of the deoxygenation of 4-dehydro-3-keto steroids it is novel that separation of the 5β- from 5α-hydrogen 3-enes formed as products is greatly facilitated by the presence of a 19-hydroxy group. Thus the isomeric 19-hydroxy-4-ene-3-ones can be more readily and quantitatively separated by chromatography than, for example, the 19-methyl, 19-acyloxy and probably 10-nor analogs, as the difference in rf-values of the 5α- and 5β-isomers is considerably greater when a 19-hydroxy is present. The isomers can also be readily separated by simple precipitation or recrystallization procedures through conversion of the product into a mixture of 5β- and 5α-hydrogen 19-formates and subsequent hydrolysis, for which a surprisingly selective procedure can be elaborated, of the formates of the 5β-series.

Generally novel about the processes of this invention using zinc and a carboxylic acid is that the latter is only employed in minimal amounts, so that, in the case of 90% aqueous formic acid less than 25 parts, when added in one lot, bring about an effective though not complete deoxygenation of saturated 3-ketones. It is surprising that if the 90% formic acid is added in small lots the deoxygenation can be fully completed with a lesser quantity of acid in less than half the time. Even smaller amounts of formic acid are needed if 4-en-3-ones are being deoxygenated. It is surprising that in the reduction the 16-dehydro-20-ketones of this invention by zinc and limited amounts of carboxylic acids, yet smaller amounts of formic acid are required, that even small amounts of acetic acid suffice, and that instead of the corresponding 20-deoxygenated products 20α-alcohols are formed in good yield.

It is advantageous that in the procedures of this invention using zinc and a limited amount of a carboxylic acid, contrary to deoxygenations by zinc described in the literature, no activation of the zinc powder, e.g. by amalgamation or pretreatment with hydrochloric acid, and heating or refluxing or cooling, respectively, of the reaction mixture is required.

While not limiting the invention to any theory, the ready deoxygenation or reduction, respectively, of ketones by zinc employing the procedures of this invention may be explained by considering a competition between the keto groups and the protons of the carboxylic acid for the active sites on the zinc surface, that in this competition the active sites are being depleted and that excess acid and an increase in temperature could lower rather than increase the ratio:

$$\frac{\text{interaction of keto group with active sites on zinc}}{\text{interaction of protons with active sites on zinc}}.$$

From this consideration it appears useful to prevent excess of acid, i.e. to use only as much acid as required for the deoxygenation process, which may consist in the adsorption of the keto group on the active sites of the zinc surface and a subsequent proton-induced desorption. The application of such considerations to the improvement of the selective deoxygenations and reductions of ketones by zinc appears to be novel despite the important role such deoxygenations and reductions play in the field of general synthetic organic chemistry and the chemistry of natural products.

Some of the 3-deoxy 14β-hydroxy cardenolides of this invention, i.e., especially 3-deoxycannogenol, have a novel biological action because they show a strong dissociation of inotropic activity from ATP-ase inhibition and lethality. This is contrary to prevailing views according to which the ratio of inotropic activity to ATP-ase inhibition and lethality remains essentially unchanged among steroids of the cardenolide and bufadienolides series. The improved cardiotonic action of 3-deoxy-14β-hydroxy cardenolides is surprising and thus, contrary to frequently expressed views that a 3-glycosyloxy group or another 3β-oxygen function promote cardiotonic action or are even indispensible for the latter action. The strong inotropic effect of 3-deoxycannogenol, i.e. 3-deoxy-19-hydroxydigitoxigenin, is also surprising as 3-deoxydigitoxigenin was found to be significantly less active than digitoxigenin and hence it appeared indicated that 3-deoxygenation generally reduces heart-activity below a therapeutically useful level. Possibly 19-hydroxylation of cardenolides of the 3-deoxy series promotes the contraction of the heart muscle even more strongly than 19-hydroxylation of 3β-oxygenated analogs.

Generally novel appears to be the application of the concept that the removal of the oxygen function in the 3-position, coupled with the introduction of β-hydroxy groups in proximity to the 14β-hydroxy butenolide moiety, can afford more active and less toxic (see also below) cardenolides.

The processes for the deoxygenation of the aglycones of naturally occurring cardenolides allow the facile preparation of 3-deoxy 14β-hydroxy cardenolides in economical yields. It is an advantage of the processes that in the preparation of the 3-deoxy 14β-hydroxy cardenolides, the 14β-hydroxy 17β-butenolide moiety remains essentially unaffected and that also other groups present in the aglycones used as starting material may remain unaffected or can be readily regenerated.

The preferred deoxygenation process, employing zinc with limited amounts of a carboxylic acid, in particular formic acid, is not only useful for the deoxygenation of 3-keto 14β-hydroxy cardenolides but also for the selective deoxygenation and selective reduction of other ketones in improved yields.

With respect to processes affording 3-deoxycannogenol, 3(4)-anhydrocannogenol and other 3-deoxy 14β-hydroxy cardenolides, it is advantageous for the oxidation of strophanthidin to strophanthidone that it can be carried out using the cheap N-bromoacetamide rather than molecular oxygen in presence of the highly expensive platinum. It is a special advantage of the process developed for the dehydration of strophanthidone to the corresponding 4-en-3-one that it can be brought about without, the isolation of the strophanthidone from the aqueous mixture by lengthy extraction procedures, does not require heating, proceeds without the use of additional organic reagents or solvents and allows the ready isolation of the reaction product, i.e. 3,19-dioxo-14-hydroxy-14β-carda-4,20(22)dienolide, in an improved yield and purity.

The reduction of the 3,19-dioxo-4-ene to the corresponding 19-hydroxy-4-en-3-one can be made to be a selective process and in the working up the product can be collected by precipitation and filtration rather than by repeated extraction with an organic solvent.

Also, the mixture of 19-hydroxy 5β- and 5α-hydrogen, formed in the special deoxygenation process with zinc and a limited amount of formic acid, can readily be separated either by chromatography, or more simply, by conversion into the corresponding 19-formates and subsequent selective hydrolysis of the 19-formyloxy 5β-hydrogen cardenolide in the mixture of isomers. It is also useful that the processes of preparing 3-deoxycannogenol comprise procedures allowing the selective hydrogenation of the double bond in the 3-position of 3(4)-anhydrocannogenol without effecting the unsaturated butenolide ring and that in turn, they also comprise special procedures allowing the selective hydrogenation of the double bond in the 4-position of 14β,19-dihydroxy-3-oxo-carda-4,20(22)-dienolide to the corresponding 5β-hydrogen 3-ketone with only very little formation of the 5α-isomer and the 20(22)-dihydro analog. It is especially useful that the 3-keto group can be selectively and completely deoxygenation under very mild conditions and that the 19-formate of 3-deoxycannogenol which is formed as a minor product, can be readily hydrolyzed to 3-deoxycannogenol without intermediate isolation of the deoxygenation product.

The two preferred conversions of strophanthidin to 3-deoxycannogenol, which comprise 6 steps each and may proceed either via 19-formyloxy-5β-carda-3,20(22)-dienolide or 19-hydroxy-3-oxo-5β-card-20(22)-enolide, can be accomplished by very simple procedures which, for example, do not require heating of reaction mixtures, and extractions and chromatographic purifications in the isolation of the products. It is also an advantage that only cheap reagents and solvents are being employed in the reactions and that none of the poisonous transition metals, which are commonly used in synthetic organic chemistry and can, even when present only in traces, devaluate a pharmaceutical product, are being used.

It is a further advantage of the processes used for preparation of 3-deoxycannogenol they that should be readily adaptable for the introduction of isotopes of hydrogen, i.e. tritium and deuterium, into a nonexchangeable position, i.e. the 3,3, the 3,5, the 3,4 or the 3,3,4,5-position respectively. Especially tritiated 3-deoxycannogenol should be useful for the assessment of the plasma levels and metabolic fate of 3-deoxycannogenol, e.g. by the radioimmunoassay. The processes described for the preparation of 3-deoxy and 3(4)-dehydrocannogenol can also be usefully adapted to the preparation of 3-deoxy 14β-hydroxy cardenolides belonging to the 19-nor series or having carboxyl functions in the 19-position. Thus it is very convenient that simple exposure of the reaction mixture, containing strophanthidone at the end of the N-bromoacetamide reaction, to fluorescent light for several hours effects the conversion of strophanthidone to the corresponding 19-carboxylic acid in high yield, and that heating of the filtrate after the zinc treatment, used for the reduction of positive bromine in the mixture, can afford the corresponding 5-(10)-en-3-one. That the latter compound, which is probably formed via the corresponding 19-carboxyl-4-en-3-one, can be readily isolated from the reaction mixture by a simple precipitation method despite the fact that none of the 3 preceding intermediates in its preparation from strophanthidin was isolated and purified, is a special utility of this oxidation process.

It is also of advantage that, owing to the special conditions used in the reduction of the positive bromine in the irradiated reaction mixture, the 19-carboxylic acid can readily be isolated, while, when the previous isolation methods are being employed, decarboxylation takes place in the final stages of the concentration of the extracts of the acidified reaction mixture.

It is useful that the above 3-oxo-14β-hydroxy cardenolides can readily be deoxygenated in the 3-position with retention of the double bond in the 5(10)- or the carboxylic acid group in the 19-position. Also, the corresponding 19-nor-4-en-3-one, which can be obtained from the 19-aldehyde analog or the isomeric 5(10)-en-3-one, can be hydrogenated to the 5β-isomer and hence 3-deoxygenated, or can be converted to the corresponding 3-ene The processes described for the preparation of 3-deoxy and 3(4)-dehydrocannogenol can further be usefully adapted to the preparation of 3-deoxy 14β-hydroxy cardenolides of the 19-methyl series from the appropriate aglycones. The adaptations used for the preparation of 3-deoxydigitoxigenin, 3-deoxydigoxigenin and 3-deoxy-12-oxodigitoxigenin are, for example, especially simple.

It is an advantage that in the selective oxidation of digoxigenin to the corresponding 3-ketone, N-bromoacetamide can be used, instead of molecular oxygen in presence of the expensive platinum, and that the N-bromoacetamide oxidation can readily, i.e. simply by prolonging the reaction time approximately 50-100 fold, be directed to yield the corresponding 3,12-diketone in preparative yield. It is further useful that digitoxigenin can be converted to 3-deoxydigitoxigenone without further purification in a much improved yield and by a very simple procedure, and that 3-dehydro and 3,12-dehydrodigoxigenin are readily and selectively deoxygenated in the 3-position with retention of their respective oxygen functions in the 12-position.

The deoxygenation conditions employing zinc and a limited amount of carboxylic acid can not only be applied to the preparation of 3-deoxy 14β-hydroxy cardenolides but also; to the deoxygenation of other alicyclic ketones and also in certain cases to the selective reduction of ketones and imines to the corresponding alcohols or amines, respectively.

In particular they may be useful for the deoxygenation of 3-keto steroids which are not 14β-hydroxy cardenolides but can afford 3-deoxy 14β-hydroxy cardenolides in subsequent reactions. Thus, the facile deoxygenation of 19-acetoxy-20β-pivaloxy-5β-pregn-8(14)-en-3-one is a key step in the preparation of 3-deoxycannogenol 19-formate from the cheap bulk steroid pregnenolone acetate. The corresponding 3-deoxy analog of the latter pregnenone is also useful for the preparation of the 8β-hydroxy, 19,8-lactone, 19,8-lactol and 8,19-oxido analogs of 3-deoxycannogenol. Among these analogs especially the 8β-hydroxy analog may have an activity which is even superior to that of 3-deoxycannogenol. For their preparation, 19-hydroxy-5β-pregn-8(14)-en-20-one may be used which has been prepared from the corresponding above 20β-pivalate in the inventor's laboratory.

Also other 3-keto steroids may by the favored deoxygenation process afford 3-deoxy analogs which are useful intermediates to 3-deoxy 14β-hydroxy cardenolides. For example, 19-hydroxy-20β-pivaloxy-5β- and 5α-pregna-3,7-diene, which are obtainable from the corresponding 4,7-dien-3-one, and 5β-pregnan-20-one may be converted to the corresponding 14β,19-dihydroxy and 14β-hydroxy 19-methyl cardenolides, respectively, by the application of processes previously developed for the partial synthesis of 3,14β-oxygenated cardenolides from the bulk steroid pregnenolone acetate.

The utility of the special deoxygenation condition is not restricted to the preparation of 3-deoxy 14β-hydroxy cardenolides and also other useful compounds may be prepared. Thus, it has been shown that the removal of the oxygen atom in the 3-position of hormonal steroids can also afford analogs with improved physiological properties. For example, 3-deoxy analogs of testosterone have received considerable attention because of modified ratios of physiological activities (see for example R. E. Counsell and P. D. Klimstra, "Medicinal Chemistry", Part II, editor A. Burger, Wiley Interscience, p. 933; S. Goedecke, M. Wenzel. Schering A. G., German Offenlegungsschrift 2 344 749, Mar. 6, 1975 and W. Cutting, "Handbook of Pharmacology," 3rd Edition, Appleton-Century-Crofts, 1967, p. 364, where 17α-ethyl-17α-hydroxyestr-4-ene "ethylestrenol," is described).

The conditions of the deoxygenation may also be useful for the deoxygenation of alicyclic ketones other than 3-keto steroids, e.g., they may be applicable to 5-en-7-keto, 8-(14)-en-15-keto, 5(10)-en-6-keto, 4-en-6- keto, 2-en-4-keto, 3-en-2-keto, 2-en-1-keto, 11-en-12-keto, 8(9)-en-7-keto and 8(9)-en-11-keto steroids and some of their saturated analogs. Generally the double bonds in the conjugated ketones would be expected to move towards the site of the keto group, e.g. to the 6-or 14(15)-position in the case of 5-en-7-ketones and 8(14)-en-15-ketones, respectively.

The conditions of the deoxygenation can further be useful for the selective reduction of certain ketones and their amines to alcohols, as evidenced by the very facile and selective reduction of 16-dehydro-20-keto steroids to the corresponding 20α-alcohols and by the reduction of the corresponding oximes. The preparation of the 16-dehydro-20α-alcohols is a very useful reaction since methods of the prior art affording 20α-alcohols are considerably less selective and since 20α-alcohols play an important role as steroid metabolites as well as in the synthesis of the highly complex and extremely cardiotoxic 16-dehydro 20α-acylate batrachotoxin, which because of its strong physiological effects, has been considered to be a valuable tool in physiological studies and to be a useful potential drug. The utility of the 16-dehydro-20α-alcohols is enhanced by the finding that the double bond in 16-position of a 5,16-dien-20α-ol can be selectively hydrogenated to the corresponding 20α-hydroxy-17α-pregn-5-ene if the hydrogenation is carried out in the presence of t-butylamine under the special conditions described above and used for the selective hydrogenation of 4-en-3-ones.

EXAMPLE 1

To a solution which consisted of 8.0 g of stophanthidin and 800 ml of 70% aqueous tertiary butanol and which was protected by an atmosphere of nitrogen, was added 9.6 g of N-bromoacetamide which had been dried in high vacuum, with swirling and exclusion of light. The mixture which was contained in a 2 liter volumetric flask covered completely with several layers of aluminium foil, was shaken at room temperature for approximately 3 hours. It was then left to stand at 24°-25° C for 42 hours whereupon 200 ml of isopropanol, followed by 240 g of zinc dust were added with swirling in the dark. The mixture was then shaken for 30 minutes, and 9.6 g of sodium bicarbonate was added to the mixture, which after the zinc treatment had completely lost its brown color. After shaking for 36 minutes the zinc dust was removed by filtration in an atmosphere of nitrogen. The zinc cake was washed with 600 ml of isopropanol and the combined filtrates were concentrated to 40 ml at reduced pressure and 160 ml of tertiary butanol was added. The mixture was again concentrated to 40 ml and another 160 ml of tertiary butanol was added. The mixture was once more concentrated to 40 ml and 160 ml of benzene was added. The mixture was yet once more concentrated to 40 ml at reduced pressure below 50° C and 320 ml of hexane was added. The mixture was concentrated till it began to become viscous whereupon 160 ml of hexane was added. The mixture was then rotated at reduced pressure with ice-cooling for approximately 10 minutes whereupon the clear supernatent hexane phase was decanted from the resinous product which consisted of strophanthidone as a major product as well as of small amounts of starting material and 3-oxo-5,14,19-trihydroxy-5β, 14β-card-20(22)-enolide, as evidenced by tlc.

The resin, which was obtained in the above oxidation and contained strophanthidone as the major steroid, was treated with 40 ml of water at room temperature at reduced pressure and then in an atmosphere of nitrogen with external ice-water cooling. It was then treated with 4.8 ml of 3.5 N aqueous hydrochloric acid, 56.0 ml of 6.01 N aqueous hydrochloric acid was added dropwise with magnetic stirring and the flask was inclined at different angles in an effort to dissolve all resinous material attached to the walls of the flask. The light yellow solution, which was 3.5 N with respect to hydrochloric acid, was then left to stand in a refrigerator at +5° C for five and a half days with intermittant seeding and stirring for several hours with ice-water cooling whereupon 30 ml of water was added slowly with stirring in an ice-water bath. The mixture, which was then 2.7 N with regard to hydrochloric acid, was left to stand at +5° for a further 3 days and 17 hours. The resulting suspension was then almost neutralized by slow addition of 335.16 ml of 1.0 N sodium bicarbonate, i.e. 0.95 moles per mole of hydrochloric acid, with external ice water cooling under nitrogen stirring of the suspension for one hour in the ice water mixture under nitrogen followed by filtration, repeated washing of the precipitate with little lots of ice-cooled water till all acid had been removed gave 6.35 g of a white powder, mp 177°-195° (evac. sealed tube), which contained 3,19-dioxo-14-hydroxy-14β-carda-4,20(22)-dienolide as the major product and small amounts of the analogous 19-alcohol and 19-carboxylic acid, as evidenced by tlc-analysis.

Another dehydration of strophanthidone, which was obtained from 6.0 g of strophanthidin, with 3.5 N hydrochloric acid was carried out very similarly as described above, except that the mixture was worked up already after two instead of five and a half days, and gave 4.132 g of product as a white powder, which consisted of 3,19-dioxo-14-hydroxy-14β-carda-4,20(22)-dienolide as the major product, contained a small amount of residual strophanthidone besides small amounts of the analogous 19-alcohol and 19-carboxylic acid, and had mp 173, 175°-178° C, nmr($CDCl_3$,δ), 5.98(1,broadened S; 4-H), 5.88(1, broadened S; 22-H), 4.88(2, broadened S; 21-H), 0.92(3,S; 18-H) and 0.73(≈0.5, S; 18-H of steroidal by-product) ppm.

Another oxidation of strophanthidine, of which 400 mg were employed, by N-bromoacetamide was carried out similarly as described above, except that the excess reagent was reduced by 10% aqueous sodium thiosulfate instead of zinc and the product was collected by several extractions of the reaction mixture with chloroform-methanol 4:1, after addition of water, an excess of solid sodium bicarbonate and of solid sodium chloride. Concentration of the dried chloroform extracts at reduced pressure with intermittant addition of hexane and filtration of the resulting suspension gave 281 mg of a white electrostatic powder, mp 121°-151° C consisting of strophanthidone as the major product and a small amount of the analogous 19-alcohol as well as of a small amount of residual strophanthidin as evidenced by tlc.

A mixture of 100 mg of the product of the above described oxidation consisting essentially of strophanthidone, 0.25 ml of glacial acetic acid and 0.25 ml of isopropanol was heated in an atmosphere of nitrogen at 100° C in a long necked flask, the stopper of which was firmly kept in place. After 1.5 hours of heating the mixture was cooled and 2.0 ml of water was added in one lot. The precipitating resin was then seeded with product another 2.0 ml of water was slowly added and the mixture was agitated under nitrogen. Subsequent filtration gave 57.6 mg of a precipitate, mp 174°-177° C, which consisted of 3,19-dioxo-14-hydroxy-14β-carda-4,20(22)-dienolide as the major product and a small amount of the corresponding 19-alcohol, as evidenced by tlc and by mnr-spectroscopy.

EXAMPLE 2

To a solution which consisted of 1.2 g of 3,19-dioxo-14-hydroxy-14β-carda-4,20(22)-dienolide, and 60 ml of dioxane-water 4:1, and was protected by an atomosphere of nitrogen and from direct light, were added successively four 0.72 ml lots of a 1% solution of sodium borohydride in the same solvent system at an interval of 10 minutes at room temperature with stirring. The reaction was monitored by tlc and 137 minutes after the addition of the first lot 0.18 ml of an additional lot of the sodium borohydride solution was added. The total number of moles of sodium borohydride added amounted to 0.277 moles per mole of starting material. The mixture was stirred for another 10 minutes whereupon the reduction was quenched by an addition of 120 ml of acetone.

Stirring was continued for 30 minutes and 270 ml of 0.1 N hydrochloric acid was added. The slightly acidic mixture was concentrated at reduced pressure to 60 ml, whereupon 60 ml of water, followed by 1.7 ml of half saturated aqueous sodium bicarbonate and 11 ml of 0.1 N hydrochloric acid were added. The slightly acidic mixture was then concentrated at reduced pressure with intermittant addition of water, toluene and hexane. Subsequent filtration of the resulting multiphasial mixture, which contained besides an aqueous suspension half a volume of hexane, gave 1.070 g of a white powder, which, after dissolution in 53.5 ml of warm acetone, cooling in ice-water, slow addition of 107.0 ml of hexane, stirring in ice and filtration, gave 0.878 g of 14,19-dihydroxy-3-oxo-14β-carda-4,20(22)-dienolide mp 218, 221°-226°, UV 218 and 238 mμ, 1R-(KBr) 3500, 3425, 3110 (shoulder, 22-H?), 3020 (4-H?), 1780, 1743, 1653, 1633, 1617, 1602, 1480, 1452, 1380, 1360, 1338, 1324, 1288, 1260, 1235, 1205, 1170, 1148, 1126, 1075, 1026, 960, 948, 892, 870, 862, 831, 773, 745, 706 and 681 cm$^{-1}$ as a white powder.

EXAMPLE 3

A solution of 100 mg of 14,19-dihydroxy-3-oxo-14β-carda-4,20(22)-dienolide in 5.0 ml of ethyl acetate was protected by an atmosphere of nitrogen, whereupon 1.0 ml of tertiary butylamine and a suspension of 20 mg of 5% palladium on charcoal in 5.0 ml of ethyl acetate were added. The mixture was then stirred at room temperature on an atmosphere of hydrogen for 131 minutes. Subsequent filtration in an atmosphere of nitrogen through a plug of cellulose fibers, which has been wetted with methanol-water 8:2, followed by evaporation at reduced pressure with intermittent addition of hexane gave 82 mg of white residue containing 14,19-dihydroxy-3-oxo-5β,14β-card-20(22)-enolide as essentially the only steroidal material, as evidenced by tlc.

A mixture of the residue obtained in the above hydrogenation, 7.5 ml of methylene chloride, 3.0 g of zinc dust which had been dried at high vacuum for 20 minutes and 2.5 ml of 90% formic acid was shaken manually for five minutes and then in a mechanical shaker overnight. Subsequent filtration followed by evaporation of the filtrate at reduced pressure with intermittent addition of toluene gave a colorless resin, which consisted of 19-formyloxy-14-hydroxy-5β,14β-card-20(22)-enolide as the major steroidal product, of a minor amount of the 19-formate of the starting material as well as of a relatively non-polar product, which was considered to be 1,19-formyloxy-5β,14β-carda-14,20(22)-dienolide, as evidenced by tlc. Dissolution of the resin in 5 ml of methylene chloride, followed by addition of 5 ml of hexane, filtration of the faintly turbid liquid through diatomaceous earth and subsequent evaporation gave 101 mg of a white residue, which was used in the subsequent hydrolysis.

To a solution, which consisted of the above product and 4.0 ml of methanol, and was protected by an atmosphere of nitrogen, was added 0.40 ml of a 4% solution of sodium bicarbonate and water. The mixture was stirred for 6 hours whereupon 0.4 ml of 3% aqueous acetic acid was added. Concentration of the neutralized mixture at reduced pressure with intermittent addition of water gave, after filtration, 69.8 mg of a white product, mp 174°-194° C, which consisted of 3-deoxycannogenol as the major product and of minor amounts of corresponding 3-keto analog and of 19-formyloxy-14-hydroxy-5α,14β-card-20(22)-enolide, the 5α isomer of the 19-formate of 3-deoxycannogenol, as evidenced by tlc. The precipitate obtained was then dissolved in 3.5 ml of methylene chloride, 1.5 ml of hexane was added and the slightly turbid liquid was filtered through diatomaceous earth. Concentration of the filtrate at reduced pressure to 2.8 ml followed by addition of 14 ml hexane, filtration and two further precipitations from methylene chloride-hexane i.e. from methylene chloride-hexane 40:60 and 50:70, respectively, gave 14.5 mg of 3-deoxycannogenol, mp 208°-211°, as a white powder, and contained the corresponding 3-ketone analog as an impurity in very small amounts, as evidenced by tlc. The latter impurity was readily removed by dissolution in methanol and precipitation of deoxycannogenol with four volumes of water.

A sample of 3-deoxycannogenol which was prepared by a procedure and was very similar to the one described above, except that the intermediate 3-ketone analog and 3-deoxycannogenol 19-formate were purified before being used in the respective subsequent reactions, had mp 209°-212° C, ir(KBr) 3506, 3444, 3110 (22-H), 2956, 2936, 2884, 2862, 1835, 1710, 1625, 1476, 1458, 1356, 1324, 1278, 1265, 1223, 1202, 1154, 1120, 1105, 1075, 1056, 1038, 1025, 956, 920, 968, 750, 712 and 700 cm$^{-1}$.

EXAMPLE 4

A solution of 240 mg of 14,19-dihydroxy-3-oxo-14β-carda-4,20(22)-dienolide in 12.0 ml of ethyl acetate was protected by an atmosphere of nitrogen, whereupon 2.4 ml of tertiary butylamine and a suspension of 48 mg of 5% palladium on charcoal in 12.0 ml of ethyl acetate was added. The mixture was then stirred at room temperature in an atmosphere of hydrogen for 98 minutes. Subsequent filtration in an atmosphere of nitrogen through a plug, which consisted of cellulose fibers and had been wetted with methanol-water 8:2, followed by concentration of the filtrate at reduced pressure gave 223 mg of a white solid which was dissolved in 12 ml of acetone with slight warming. Concentration at reduced pressure to 1.2 ml gave, after seeding, a white suspension to which 1.5 ml of hexane was slowly added dropwise with stirring at room temperature. After approximately 3 hours of further stirring the suspension was filtered and the precipitate obtained was washed successively with small lots of hexane-acetone 2:1 and hexane yielding 189 mg of 14,19-dihydroxy-3-oxo-5β,14β-card- 20(22)-enolide, mp 218, 222°–225° C, as a white powder which was used for the reaction described in the following example.

A sample of the latter 5β-hydrogen-3-ketone which was obtained in another reaction by a procedure, which was very similar to the one described above, had mp 211°, 223°–230° C and ir(KBr) 3550, 3480, 2930, 2872, 2855, 1727, 1620, 1434, 1380, 1344, 1283, 1258, 1200, 1173, 1140, 1100, 1020, 965, 896, 862, 768 and 738 cm$^{-1}$.

EXAMPLE 5

To a mixture of 80.0 mg of 14,19-dihydroxy-3-oxo-5β,14β-card-20(22)-enolide, 1.6 g of glass beads, which had a diameter of 3 mm, 2.4 g of zinc dust, which had been dried at high vacuum, 6.0 ml of methylene chloride, which had been dried over 4 Å molecular sieves, were added eight lots of 0.080 ml each of 90% formic acid at a time interval of 20 minutes. Each individual lot of formic acid was added dropwise with intermittent swirling. After each addition the mixture was mechanically shaken for 20 minutes; 20 minutes after the last addition the mixture was externally cooled in ice-water whereupon 4.0 ml of methanol was added with agitation. The stopper of the reaction flask was firmly fixed and the mixture was shaken in the ice-water for approximately 2 hours and was then left to stand in a refrigerator at +5° for 16 hours. The stopper was then removed carefully to allow a gradual release of the moderate pressure, which can develop during the methanol treatment, the remaining zinc was removed by filtration and the mixture was concentrated three times to 1.6 ml with intermittent addition of 8.0 ml each of methanol.

The methanolic solution was diluted with 6.4 ml of methanol and 8 lots of 0.4 ml of freshly prepared 1N aqueous sodium bicarbonate were added. To the resulting barely alkaline mixture, which was stirred under nitrogen, 4 additional lots of 0.4 ml of the 1N sodium bicarbonate solution were then added at 15 minutes interval, followed by a fifth 0.4 ml lot 2 hours after the fourth addition and after tlc-analysis of sample taken from the mixture 60 min. after the latter addition. The mixture was stirred for 3 more hours and then left to stand under nitrogen at +5° for 16 hours whereupon 1.0 ml of 2N of aqueous acetic acid was added in one 0.5 ml and two 0.25 ml lots. The mixture which was then no longer basic, was three times concentrated to 1.6 ml at reduced pressure with intermittent addition of 1.6 ml each of water. Subsequent filtration gave 78 mg of a white precipitate which was dissolved in 10.92 ml of acetone-methylene chloride 1:1, briefly stirred with 39 mg of diatomaceous earth and filtered.

Concentration to 0.78 ml, followed by slow addition of 4.0 ml of hexane to the resulting suspension, which was stirred under nitrogen, 4 hours of further stirring and filtration gave 49.95 mg of a white precipitate, mp 193°–199° C, which, after dissolution in 3.7 ml of methylene chloride, precipitation by slow addition of 2 volumes of hexane, approximately 3 hours of further stirring and filtration gave 37.0 mg of 3-deoxycannogenol, mp 208°, 210°–211° C, nmr (CD$_3$ODδ), 5.90 (1, broadened S; 22-H), 4.97 (2, broadened S; 21-H), 3.63 (2, d, d, J 10 Hz; 19-H), 2.63-3.04 (m; 17-αH) and 0.87 (3, S; 18-H) ppm as a white powder.

EXAMPLE 6

A mixture of 8.0 mg 14,19-dihydroxy-3-ox-5β,14β-card-20(22)-enolide 0.6 ml of methylene chloride, 240 mg of zinc dust and 1.8 ml of 90% formic acid was shaken at room temperature for 16 hours, whereupon 1.5 ml of ethyl acetate and 0.3 ml of water were added. The mixture was shaken for 10 minutes and then filtered. The organic phase of the filtrate was washed thrice with 0.8 ml of water and then evaporated. Chromatography on silica gel G coated glass-plates with ethyl acetate-benzene 1:1, followed by recrystallization of the fraction isolated with etherpentane gave 2.9 mg of 3-deoxycannogenol 19-formate, mp 150°–151° C, as verified by comparison of its ir-spectrum with that of the compound obtained by partial hydrogenation of 3(4)-anhydrocannogenol and subsequent formylation (see Example 11).

EXAMPLE 7

A mixture of 5 mg of 14,19-dihydroxy-3-oxo-5β,14β-card-20(22)-enolide, 5 mg of tosylhydrazine was shaken under nitrogen at room temperature for 90 minutes whereupon it was evaporated at reduced pressure. The residue which was considered to consist essentially of the 3-tosylhydrazone of the starting material, as also indicated by tlc analysis, was then treated with a solution, which was cooled in an ice-methanol bath below 0° C and consisted of 0.25 ml of methanol and 10.0 mg of sodium borohydride. The mixture was shaken at room temperature for 1.5 hours whereupon 0.25 ml of acetone was added. The mixture was left to stand for one hour, acidified with 1.75 ml of 0.1N aqueous hydrochloric acid and neutralized with 0.03 ml of half-saturated sodium bicarbonate. It was then evaporated at reduced pressure to yield a product considered to consist mainly of 3-deoxycannogenol and a smaller amount of cannogenol. The latter product, 0.225 ml of methylene chloride and 0.075 ml of 90% formic acid was shaken under nitrogen for 16 hours and evaporated to yield a product containing 3 dexoycannogenol 19-formate, as evidenced by comparison of its thin layer chromatogram with that of a product obtained by direct 3-deoxygenation of 14β,19-dihydroxy-3-oxo-5β-card-20(22)-enolide with zinc and formic acid (see preceding Example).

EXAMPLE 8

To a solution of 100.0 mg of 14,19-dihydroxy-3-oxo-14β-carda-4,20(22)-dienolide, which had been dried in high vacuum, in 7.5 ml of methylene chloride, which had been dried over 4 Å molecular sieves, was added successively 3.0 g of zinc dust, which had been dried in high vacuum, and 2.5 ml of 90% formic acid with manual swirling of the reaction mixture. The reaction mixture was then shaken mechanically for 18 hours at room temperature and filtered. The filtrate was concentrated at reduced pressure and the residual formic acid was removed by intermittent addition of toluene. Dissolution of the resultant white resin in a small amount of methylene chloride, followed by concentration at reduced pressure with intermittent addition of hexane and subsequent filtration yielded 99.0 mg of a white powder consisting of a mixture of 3(4)-anhydrocannogenol 19-formate, which was present as the major product and was selectively hydrolyzed in the next reaction, and of a smaller amount of the corresponding 5α-isomer, 3(4)-anhydrocoroglaucigenin 19-formate.

To a solution of the 99 mg of a total product, which was obtained in the preceding reaction, in 3.96 ml of methanol was added 0.198 ml of a 2% aqueous solution of sodium bicarbonate under nitrogen. The reaction mixture was stirred for four and a half hours at room temperature whereuon it was neutralized with 0.198 ml of 3% aqueous acetic acid. The methanol in the reaction mixture was removed by concentration at reduced pressure with intermittent addition of ethyl acetate. Subsequent four-fold extraction with water, drying of the organic phase with anhydrous sodium sulfate, filtration and evaporation at reduced pressure and dissolution of the resulting white foam in 0.80 ml of methylene followed by slow addition of 4.0 ml of hexane, agitation for 2 hours at room temperature and filtration gave 50 mg of 14,19-dihydroxy-5$\beta$,14$\beta$-carda-3,20(22)-dienolide(3(4)-anhydrocannogenol) as a white powder, as indicated by tlc. Tlc-analysis also indicated the presence of 3(4)-anhydrocoroglaucigenin 19-formate and a small amount of 3(4)-anhydrocoroglaucigenin in the mother liquors.

EXAMPLE 9

To a solution of 23.0 mg of 14,19-dihydroxy-5$\beta$,14$\beta$-carda-3,20(22)-dienolide in 0.8 ml of methanol was added 6.25 mg of 5% palladium on carbon suspended in 1.6 ml of methanol under nitrogen. The reaction mixture was stirred in an atmosphere of hydrogen for 55 minutes at room temperature, whereupon the hydrogen was replaced by nitrogen. Filtration through cellulose tissue, which had been wetted with methanol-water 10:1, in an atmosphere of nitrogen followed by evaporation of the filtrate at reduced pressure, dissolution of the product in 0.7 ml of methylene chloride, slow addition of 1.5 volumes of hexane, shaking for 1 hour under nitrogen and filtration gave 13.8 mg of product as a white powder, which after combination with 14.3 mg of another batch which was similarly obtained, dissolution in 1.4 ml of methylene chloride, addition of 0.35 ml of hexane, filtration of the slightly turbid liquid through diatomaceous earth, evaporation to dryness, dissolution in 1.12 ml of methylene chloride, slow addition of 1.5 volumes of hexane, shaking under nitrogen for 1 hour and filtration gave the 20 mg of 3-deoxycannogenol, mp 210°–213° C.

EXAMPLE 10

A mixture of 50 ml of methylene chloride and 10 ml of 90% formic acid was shaken well, whereupon the methylene chloride saturated with formic acid was separated and mixed with an equal volume of methylene chloride. A mixture of 180 mg of 14,19-dihydroxy-3-oxo-14$\beta$-carda-4,20(22)-dienolide, 13.5 ml of methylene chloride, 514 g of zinc dust and 40.5 ml of the methylene chloride, which was half-saturated with formic acid as described above, was shaken for 80 minutes in a 250 ml volumetric flask. The mixture was filtered and the filtrate was neutralized with 33.8 ml of aqueous half-saturated sodium bicarbonate solution. The organic phase was dried with anhydrous sodium sulfate and then evaporated at reduced pressure with intermittent addition of hexane. The product was chromatographed on silica gel G coated glass-plates with ethyl acetate-benzene 2:1. Two recrystallizations of the major fraction with methylene chloride-hexane gave 66 mg of 3(4)-anhydrocannogenol, mp 180°–184°; nmr($\delta$) 5.91 (1, broadened S or unresolved dd or t; 22-H), 5.15-5.85 (2, m, 3—H, 4—H), 4.92 (2, broadened S or dd, 21—H), 3.74 (2, dd, 19—H) and 0.91 (3, S, 18—H ppm; ir(KBr) 3420 (broad, strong), 3095, 3016, 2959, 2930, 2915, 2896, 2852, 2832, 1801, 1738, 1715, 1615, 1436, 1363, 1305, 1174, 1123, 1070, 1019, 934, 865, 811, 740 and 678 cm$^{-1}$. Recrystallization of a minor, slightly less polar fraction with the same solvent system afforded the 5$\alpha$-hydrogen isomer 3(4)-anhydrocoroglaucigenin, mp 217°–224°.

EXAMPLE 11

A mixture of 20 mg of 3(4)-anhydrocannogenol and 0.67 ml of methanol was protected by a nitrogen atmosphere, whereupon a suspension of 5 mg of 5% palladium on charcoal in 1.33 ml of methanol was added. The nitrogen was then replaced by hydrogen, and the mixture was stirred at atmospheric pressure. Maintenance of atmosphere pressure was ensured by a hydrogen filled gas-burette, which was connected to the reaction vessel. After 60 minutes of stirring the hydrogen was replaced by nitrogen and the mixture was filtered through a tissue paper plug (Kim Wipe) under nitrogen. Evaporation of the filtrate at reduced pressure, followed by chromatography of the residue obtained on silica gel G coated glass-plates with ethyl acetatebenzene 1:1 as the eluant gave 10.31 mg of a major fraction, which after dissolution in 0.1 ml of methylene chloride and precipitation with 0.8 ml of hexane gave 8.01 mg of 3-deoxycannogenol, mp 209°, 211°–212°.

Also collected was a chromatographic fraction, which was slightly more polar than the major fraction, and contained mainly the 3,4,20,22-tetrahydro product in addition to the 3,4-dihydro product, 3-deoxycannogenol. The more polar fraction was then combined with a similar fraction obtained from a preceding run and hydrogenated similarly as described above except that the hydrogenation time was prolonged approximately 16 fold. Recrystallization of the residue obtained after evaporation of the filtrate from hexane-methylene chloride gave 5.03 mg of 3-deoxy-20$\xi$,22-dihydrocannogenol, mp 195°–199°, ir(KBr) 3515, 2915, 2875, 2845, 1762, 1620 (shallow), 1472, 1450, 1412, 1380, 1360, 1340, 1242, 1220, 1195, 1185, 1165, 1148, 1100, 1019, 1005, 943, 900, 885, 846, 805, 750 and 670 cm$^{-1}$.

Agitation of 1.67 mg of a sample of 3-deoxycannogenol which was obtained by a procedure similar to the one described above with 0.15 ml of methylene chloride and 0.050 ml of 90% formic acid for 23 hours followed by addition of 0.25 ml of toluene, evaporation of the mixture at reduced pressure, chromatography of the residue on silica gel G coated glass-plates with ethyl acetate-benzene 1:1, dissolution of the isolated fraction in ether and precipitation with pentane gave 3-deoxycannogenol 19-formate, mp 152°–158°, ir(KBr) 3568, 3455, 2930, 2895, 2850, 1774, 1750, 1740, 1705, 1623, 1467, 1442, 1375, 1335, 1296, 1255, 1170, 1075, 1018, 949, 896, 845 and 685 cm$^{-1}$.

EXAMPLE 12

A mixture prepared by successive addition of 75 g of zinc dust, 187.5 ml of methylene chloride and 62.5 ml of 90% formic acid to 2.5 g of 19-acetoxy-20$\beta$-pivaloxy-pregn-8(14)-en-3-one was shaken at room temperature for 16 hours, whereupon it was filtered. The collected metallic residue was washed repeatedly with methylene chloride and the combined filtrates were concentrated at reduced pressure with intermittent addition of ether and external warming by a water-bath having a temperature between 25°–35° C; 150 ml of water was then added and the mixture was rotated at reduced pressure for 15 minutes. Filtration, washing with water, followed by drying on high vacuum gave 2.35 g of a white precipitate. Dissolution of the latter in methylene chloride, concentration at reduced pressure with intermittent addition of methanol, precipitation by slow addition of approximately one volume of water in a nitrogen atmosphere, filtration, washing with aqueous methanol and drying gave 2.291 g of 19-acetoxy-20β-pivaloxy-5β-pregn-8(14)-ene, mp 120°-123°.

The above reduction has also been described in United States Patent Application Ser. No. 497,729, filed August 15, 1974, Example 85. The conversion of the product to 3-deoxycannogenol 19-formate has been described in Examples 85, 86 and 87 of the above-mentioned application as well as in Examples 42, 43 and 44 of British Patent Application Ser. No. 50262/74, filed Nov. 20, 1974. Deoxycannogenol 19-formate prepared as above had mp 158-158.5°; m/e 402, 384, 356 and 325; its structure was confirmed by the comparison of its ir-spectrum with that of the product obtained by the partial hydrogenation of 3(4)-anhydrocannogenol and subsequent formylation, (see Example 11).

EXAMPLE 13

A mixture of 2.0 mg of 3-deoxycannogenol, 2.0 mg of isopropylidene malonate and 0.04 ml of methyl isobutyl ketone was heated under nitrogen in an oil-bath having a temperature of 76° for 4 hours whereupon the solvent was evaporated at reduced pressure. Tlc analysis indicated that the product contains a trace of starting material besides the major product 3-deoxycannogenol 19-hemimalonate. Treatment of the product with ethereal diazomethane gave the methyl ester of the above hemimalonate, as indicated by tlc analysis.

EXAMPLE 14

A mixture of 2.5 mg 3(4)-anhydrocoroglaucigenin, 0.18 ml of methylene chloride and 0.06 ml of 90% formic acid was shaken for 16 hours whereupon it was evaporated with the help of nitrogen, reduced pressure and intermittent addition of toluene. The resulting residue, which contained the 19-formate of the starting material as practically the only steroid, as evidenced by tlc analysis, was then dissolved in methanol-ethyl formate 85:15. The mixture was protected by a nitrogen atmosphere and 0.55 mg of 5% palladium on charcoal was added. The nitrogen atmosphere was replaced by hydrogen and the mixture was shaken for 60 minutes. Subsequent filtration in a nitrogen atmosphere followed by evaporation, chromatography of the residue on silica gel G and recrystallization from methylene chloride-hexane gave 1.19 mg of 3-deoxycoroglaucigenin 19-formate, mp 204°-205°, ir(KBr) 3482, 2921, 2855, 1772, 1730, 1690, 1622, 1478, 1441, 1378, 1331, 1246, 1200, 1135, 1105, 1072, 1022, 951, 881, 853, 815, 729 and 680 cm$^{-1}$, as further verified by comparison of its ir-spectrum and its thin layer chromatogram with that of the product obtained from pregnenolone acetate as described in British Patent Application Ser. No. 50262/74, filed Nov. 20, 1974.

EXAMPLE 15

To a solution, which consisted of 250.0 mg of strophanthidin and 25.0 ml of 70% aqueous tertiary butanol, was contained in a 250 ml volumetric flask and was protected by an atmosphere of nitrogen, was added 300.0 mg of N-bromoacetamide which had been dried in high vacuum, with swirling and careful exclusion of light. The reaction flask, which was completely covered with several layers of aluminium foil, was shaken at room temperature for approximately 4 hours and was then left to stand at 23°-25° C for 2 days and overnight in a refrigerator at +5° C. Tlc analysis of a sample of the clear, brown reaction mixture indicated that nearly all starting material had been converted to 3,19-dioxo-5,14-dihydroxy-5β,14β-card-20(22)-enolide and into a small amount of corresponding 19-carboxylic acid.

The brown solution was then exposed to the fluorescent light, with which the laboratory was illuminated, for approximately 3.5 hours with gentle shaking whereupon 2 samples equivalent to 10 mg of steroid each were taken and the mixture was frozen in dry ice. After tlc analysis, which indicated that most of the 19-aldehyde had been corverted to the corresponding 19-carboxylic acid, the mixture was thawed, and 6.9 g of zinc dust was added, the mixture was shaken in a water bath at room temperature for half an hour, 276.0 mg of sodium bicarbonate was added and the mixture was shaken for 10 minutes. The decolorized mixture, which had been stored in dry ice overnight, was thawed, filtered and the zinc residue was washed with 22.0 ml of isopropanol, the combined filtrate and washings were concentrated at reduced pressure with minimal heating to 1.1 ml and 4.4 ml of benzene was added. The mixture was concentrated 5 times to 1.1 ml with intermittent addition of 4.4 ml of benzene after each concentration. Finally 12.0 ml of benzene was added, the mixture was then stored at −5° C.

The partially frozen mixture, which was obtained in the above oxidation and contained still the 19-carboxylic and as a major product and insignificant amounts of non-acidic decarboxylated material, as evidenced by tlc, was then thawed and freed from solvent by evaporation at reduced pressure. The resin obtained, which was considered to contain 175.0 mg of steroidal material, was then stirred with 13.12 ml of methylene chloride, 5.25 g of zinc dust and 4.3 ml of 90% formic acid for 2 hours at room temperature, whereupon the mixture was diluted with equal volume of methylene chloride. Filtration with minimal air exposure followed by concentration at reduced pressure with intermittent addition of toluene gave a yellow resin consisting essentially of 19-carboxy-14-hydroxy-5β,14β-carda-3,20(22)-dienolide, of a minor amount of a less polar product, considered to be the 5α-isomer and of a substantial amount of a more polar acid, as evidenced by tlc. The mixture was then dissolved in 21.86 ml of chloroform (125 parts), the chloroform solution was extracted once with half a volume of half-saturated aqueous sodium bicarbonate, the separated aqueous phase was extracted four times with an equal volume of chloroform and the combined organic extracts were dried with anhydrous sodium sulfate. Subsequent evaporation of the dried organic extracts at reduced pressure at 30° C gave a resin which by tlc had the same composition as the product above except that the more polar acid had been removed.

A mixture of the above product in 11.6 ml of an ethereal solution of diazomethane was left to stand at +5° C for 15 minutes whereupon it was evaporated with a stream of nitrogen. Chromatography of the product on glass plates coated with silica gel G, using ethyl acetate-benzene, 1:2 as the eluent, gave 27.18 mg of a major fraction which after treatment with hexane gave 22.0 mg of a white precipitate considered to be 19-methoxycarbonyl-14-hydroxy-5β,14β-carda-3,20(22)-dienolide, nmr (CDCl$_3$,δ) 5.85(1, broadened S; 22—H), 5.13-5.93 (2, m or broadened dd; 3—H, 4—H), 4.87 (2, partially resolved d.d; 21—H), 3.66 (3, S; O-CH$_3$), 2.43-3.97 (m; 17α-H), 0.93 (3, S; 18—H) ppm, ir(KBr) 3540, 3520, 3500, 3470, 3100 (22—H?), 3005 (3—H, 4—H), 1782, 1734, 1720, 1622, 1615, 1470, 1455, 1438, 1395, 1336, 1295, 1272, 1244, 1200, 1171, 1140, 1113, 1095, 1070, 1040, 1015, 990, 970, 938, 890, 845, 768, 735, 685 and 660 cm$^{-1}$.

EXAMPLE 16

A mixture of 500.0 mg of 3,19-dioxo-14-hydroxy-14β-carda-4,20(22)-dienolide in 50.0 ml of acetone — 30% aqueous hydrogen peroxide — 0.05% aqueous sodium bicarbonate 100:1:5 was stirred under nitrogen for 20 minutes whereupon it was concentrated to 2.5 ml at reduced pressure. Rotation under vacuum with intermittent addition of a total of 20 ml of water and subsequent cooling in ice-water gave, after filtration and disintegration of the brittle lumps in the mixture, 287.0 mg of a faintly yellow precipitate, mp 130°-142°, 150° C, nmr (CDCl$_3$,δ) 11.18 (1, S; 19—H), 5.73-6.50 (2, m or broad S, exchangeable; 19—OH or 19—OOH, 14—OH?), 4.97 (2, broadened d; 21—H), 3.04 (~0.5, S; 4β—H), 0.97 (3, S; 18—H) ppm, ir(KBr) 3400, 2935, 2860, 1775, 1735, 1720, 1708, 1610, 1445, 1400, 1340, 1300, 1250, 1246, 1170, 1135, 1070, 1021, 952, 890, 878, 860, 820, 780, 735 and 695 cm$^{-1}$, which was considered to be 3,19-dioxo-5β-hydroxy-14-hydroxy-14β-card-20(22)-enolide 19,5-lactole or the analogous 19-hydroperoxy-19,5-lactol.

A solution of 2.0 mg of a product which had been prepared by addition of hydrogen peroxide to 3,19-dioxo-14-hydroxy-14β-carda-4,20(22) dienolide by the method, which was similar to the one described above, in 0.2 ml of acetone was irradiated by a 60 watt lamp from a distance of 10 cm at 35° C for 4-5 days, whereupon it was evaporated. Tlc analysis showed that an unknown rather polar acid had been formed as the major product. Treatment of the latter product with zinc, methylene chloride and formic acid as described in the preceding Example gave a less polar acid as the major product. The latter acid was identical by tlc with 19-carboxy-14-hydroxy-5β,14β-carda-3,20(22)-dienolide, the preparation of which had been described in the preceding Example. Subsequent treatment of the acid obtained with an ethereal solution of diazomethane at −5° C for 15 minutes gave a product containing 19-methoxycarbonyl-14-hydroxy-5β,14β-carda-3,20(22)-dienolide as evidenced by tlc comparison with the methyl ester obtained in the preceding Example.

EXAMPLE 17

A mixture of 100 mg of 3,19-dioxo-14-hydroxy-14β-carda-4,20(22)-dienolide, 7.5 ml of methylene chloride and 60 ml of a solution of 90% formic acid in methylene chloride, which had been prepared by mixing methylene chloride - 90% formic acid 5:1, separation of the lower phase and dilution of the latter with one volume of methylene chloride, and 3.0 g of zinc dust was shaken for 40 minutes at room temperature, whereupon it was filtered. Neutralization of the filtrate with aqueous sodium bicarbonate, drying of the organic phase with sodium sulfate, evaporation at reduced pressure, chromatography of the residue obtained on glass-plates coated with silica gel G, using ethyl acetate as the eluant, gave a major fraction which had nmr (CDCl$_3$,δ) 5.90 (1, broadened S; 22-H), 5.33 (~0.5, S;?), 4.94 (2, broadened S; 21—H), 3.31 (~0.5, S; 4β—H), 2.57-3.03 (m; 17α—H) and 0.91 (3,S; 18—H) ppm. A sample which was similarly prepared in another reaction and was identical by tlc with the above product, had, after digestion of the isolated fraction with hexane, mp 147°-149° C, UV(CH$_3$OH) 219 mμ, ir(KBr) 3520, 3480, 3100 (22-H?), 3067, 2950, 2865, 1785, 1745, 1725, 1715, 1640, 1445, 1418, 1386, 1346, 1316, 1280, 1208, 1188, 1128, 1076, 1030, 965, 912, 900, 882, 860, 831, 734, 714 and 700 cm$^{-1}$ and m/e 400 (molec. ion +CH$_2$?), 386 (molec. ion ?), 384, 386, 372 (molec. ion −CH$_2$?) and appeared thus to be a, possibly rearranged, dihydro analog of the starting material rather than the expected mixture of 14β-hydroxy-19-oxo-5β,14β-carda-3,20(22)-dienolide and its 5α-isomer.

EXAMPLE 18

A mixture of 250 mg of 14β-hydroxy-3,19-dioxocarda-4,20(22)-dienolide and 5.0 ml of methanol was stirred under nitrogen, whereupon 11 lots of 0.125 ml of 0.5 N methanolic potassium hydroxide, i.e. a total of 1.375 ml corresponding to 1.061 moles potassium hydroxide per mole starting material were added at an interval of 10 minutes. About 90 minutes after the first addition of the potassium hydroxide 0.50 ml of glacial acetic was added, followed by 5.0 ml of water. The mixture was concentrated to 2.5 ml at reduced pressure, 2.5 ml of water was added and the mixture was again concentrated to 2.5 ml. The latter addition and concentration were repeated once and 2.5 ml of water was added. The mixture was stirred in ice-water for some time and was then filtered, yielding 187 mg of a precipitate consisting essentially of 14-hydroxy-3-oxo-19-nor-14β-carda-4,20(22)-dienolide, as evidenced by tlc and by the transformations described in the following four Examples. The assessment of the degree of conversion of the 19-aldehyde, which is used as the starting material, to the 19-nor 4-en-3-one, which is formed as the product by tlc is difficult, as the starting material and the product have very similar rf-values. It was found possible, however, to assess the degree conversion by treatment of the neutralized samples with zinc and formic acid employing for example the method described in Example 21, since the products formed from the 19-aldehyde and 19-nor analog by this treatment have rather different rf-values as evident from Examples 19 and 21, respectively. The ir spectrum of a sample in KBr of a batch, which was similarly prepared by slow addition of slightly more than 1 mole of potassium hydroxide per mole starting material, had peaks at 3560, 3450 (broad), 3078 (small, 22—H), 3004 (small, 4—H?), 2930, 2855, 1775, 1730, 1645, 1618, 1602, 1432, 1332, 1251, 1205, 1165, 1124, 1100, 1060, 1028, 946, 880, 840, 810, 738 and 670 cm$^{-1}$.

Tlc of samples, which were neutralized by acetic acid and taken before all the potassium hydroxide had been added, indicated the presence of the isomeric 5(10)-en-3-one, which probably is isomerized to the 4-en-3-one by the subsequently added lots of potassium hydroxide.

EXAMPLE 19

A mixture of 50 mg of 14β-hydroxy-3-oxo-19-norcarda-4,20(22)-dienolide, 5.0 ml of ethyl acetate, 0.5 ml of tertiary butylamine and 10 mg of 5% palladium on charcoal was magnetically stirred in an atmosphere of hydrogen for 2 hours, whereupon the catalyst was removed by filtration in an atmosphere of nitrogen. Evaporation at reduced pressure gave a material which after two recrystallizations, of which the final one was from acetonewater 1:4, afforded 21.1 mg of a white precipitate considered to be 14β-hydroxy-3-oxo-19-nor-5β-card-20(22)-enolide. Thin layer chromatography of samples taken after 20 minutes and after 2 hours indicated that after 20 minutes about 40% of the starting material had been converted to the product and that after 2 hours all of the starting material had disappeared.

EXAMPLE 20

A mixture of 20 mg of the purified product obtained in the preceding hydrogenation, 1.5 ml of methylene chloride, 600 mg of zinc powder and 0.5 ml of 90% formic acid was shaken overnight, whereupon it was diluted with 1.5 ml of methylene chloride and filtered. The zinc residue was washed with 3.0 ml of methylene chloride. Evaporation of the combined filtrate and washings at reduced pressure with intermittent addition of toluene gave a colorless resin which was chromatographed on silica gel G coated glass plates with ethyl acetate-benzene 1:1 as the eluant yielding 8.85 mg of a major fraction, 1.49 mg of a less polar fraction, and 0.36 mg of a more polar fraction, considered to be starting material, as evidenced by tlc. Dissolution of the major fraction in methanol and addition of a half volume of water gave a white precipitate, mp 125, 128°–131° C, ir(KBr) 3425, 2905, 2838, 1795, 1775, 1732, 1612, 1440, 1386, 1372, 1334, 1306, 1275, 1210, 1156, 1127, 1061, 1023, 981, 948, 894, 848, 823, 733 and 690 cm$^{-1}$, considered to be 14$\beta$-hydroxy-19-nor-5$\beta$-card-20(22)-enolide. The less polar fraction was digested with hexane and yielded then a precipitate, ir(KBr) 2920, 2840, 1789, 1759, 1624, 1433, 1372, 1270, 1249, 1170, 1130, 1012, 888 and 842 cm$^{-1}$, which possibly could be 19-nor-5$\beta$-card-14,20(22)-dienolide.

EXAMPLE 21

A mixture of 90 mg of 14$\beta$-hydroxy-3-oxo-19-norcarda-4,20(22)-dienolide, 6.750 ml of methylene chloride, 2.7 g of zinc powder and 2.250 ml of 90% formic acid was shaken for 15 min, whereupon it was diluted with 6.75 ml of methylene chloride and filtered with a minimum of air exposure. The zinc cake was washed with 13.5 ml of methylene chloride-acetone 1:1, the filtrate and the washings were combined and evaporated at room temperature at reduced pressure. The final evaporation of residual amounts of formic acid was carried out at high vacuum and the formic acid vapors were trapped by potassium hydroxide. Tlc analysis showed that practically only a single product had been formed after 5 minutes of reaction time, while an additional less polar product had been formed in moderate amounts after 15 minutes of shaking. Chromatography of the residue obtained on silica G coated glass plates with ethyl acetate-benzene 1:1 as the eluant gave 60.07 mg of a major fraction and 36.59 mg of an additional less polar fraction. Digestion of the major fraction with hexane followed by precipitation from methanol-water 2:1 gave a product, which had only a single spot on tlc and was considered to be 14$\beta$-hydroxy-19-nor-5$\beta$-carda-3,20(22)-dienolide, ir(KBr) 3500, 3002 (3-ene ?), 2942, 2918, 2844, 1789, 1732, 1723, 1621, 1465, 1446, 1430, 1379, 1340, 1291, 1255, 1170, 1026, 960, 892, 856, 736 and 672 cm$^{-1}$, mp 174° (shrinking), 185°–192° C, which possibly still contained a small amount of the 5$\alpha$-isomer.

EXAMPLE 22

A mixture of 50 mg of 14$\beta$-hydroxy-19-nor-5$\beta$-carda-3,20(22)-dienolide, 5.0 ml of methanol and 12.5 mg of 5% palladium on charcoal was stirred magnetically in an atmosphere of hydrogen for 50 minutes, whereupon it was filtered. The filtrate was concentrated and the residue was chromatographed on silica gel G coated glass plates with ethyl acetate-benzene 1:1 as the eluant. Digestion of the major fraction with hexane gave, after filtration, 20 mg, mp 124°, 125°–130° C, of a white precipitate. Dissolution of 15 mg of the latter in 0.15 ml of methanol followed by addition of 0.30 ml of methanol-water 1:1 yielded 13.22 mg of a precipitate, ir(KBr) 3500, 3450, 2905, 2830, 1795, 1782, 1732, 1719, 1620, 1462, 1440, 1387, 1338, 1306, 1253, 1212, 1160, 1128, 1061, 1022, 960, 942, 892, 849, 823, 732 and 690 cm$^{-1}$, which consisted essentially of 14-hydroxy-19-nor-5$\beta$,14$\beta$-card-20(22)-enolide and contained a small amount of starting material as indicated by the ir-spectrum. Tlc analysis of the crude product indicated the presence of a product which was slightly more polar than the major product and was considered to be 14-hydroxy-19-nor-5$\beta$,14$\beta$,20$\xi$-cardanolide.

EXAMPLE 23

Strophanthidin, of which 1.0 g was used, was oxidized by N-bromoacetamide in the dark and then in the presence of light employing a procedure which was similar to the one described in Example 15. The filtrate, which was obtained after the treatment with zinc dust and sodium bicarbonate, and contained 19-carboxy-5,14-dihydroxy-3-oxo-5$\beta$,14$\beta$-card-20-(22)-enolide as the major steroid as well as 100 ml of isopropanol, 70 ml of tertiary butanol, 30 ml of water and acetamide, was heated under nitrogen at 71° C for 17.5 hours, whereupon the mixture was concentrated to 5.0 ml at reduced pressure. The mixture was protected by an atmosphere of nitrogen, 50 ml of water was added slowly and lumps, which had formed during the addition, were broken up. Concentration to half a volume at reduced pressure, followed by rotation under vacuum in ice-water and filtration gave 474 mg of a yellowish precipitate, mp 197°–203° C, consisting essentially of 14$\beta$-hydroxy-3-oxo-14$\beta$-carda-5(10),20(22)-dienolide, besides some polar byproducts, as evidenced by tlc.

EXAMPLE 24

To a mixture of 60 mg of the product of the preceding reaction, which consisted essentially of 14-hydroxy-3-oxo-14$\beta$-carda-5(10),20(22)-dienolide, 4.5 ml of methylene chloride, which had been stored over 4 Å molecular sieves, 1.2 g of glass beads, which had a diameter of 3 mm, and 1.8 g of zinc dust, which had been dried on high vacuum, were added seven lots of 0.12 ml each of 90% formic acid at time intervals of 20 minutes. Each lot was added dropwise with intermittent swirling. After each addition the mixture was shaken mechanically for 20 minutes. Twenty minutes after the last addition 3.0 ml of acetone was added and the mixture was again shaken for 20 minutes. Subsequent filtration with a minimum of air exposure, addition of 1 N sodium bicarbonate till the mixture was just alkaline, neutralization of the small excess of alkali with small lots of 2N aqueous acetic acid, concentration at reduced pressure to 3.0 ml, addition of 3.0 ml of water, another concentration to 3.0 ml and filtration gave 48 mg of an off-white precipitate, which after dissolution in methylene chloride, replacement of the lattery by concentration at reduced pressure and intermittent addition of hexane and filtration gave 21 mg of 14-hydroxy-19-nor-14$\beta$-carda-5(10),20(22)-dienolide, mp 195°–200° C, ir(KBr) 3504, 3128 (22-H?), 2973, 2940, 2915, 2848, 1792, 1724, 1625, 1466, 1450, 1431, 1389, 1365, 1343, 1295, 1255, 1220, 1203, 1170, 1132, 1118, 1090, 1075, 1030, 1010, 995, 965, 925, 896, 857, 839, 690 and 657 cm$^{-1}$, nmr(CDCl$_3$,$\delta$) 5.88 (1, broadened S, 22—H), 5.70 ($\sim$0.5, broadened S,?), 593 (2, incompletely resolved dd, 21—H), 2.5-2.96 (m, 17α—H) and 0.90 (3, S, 18—H) ppm, as a white powder.

EXAMPLE 25

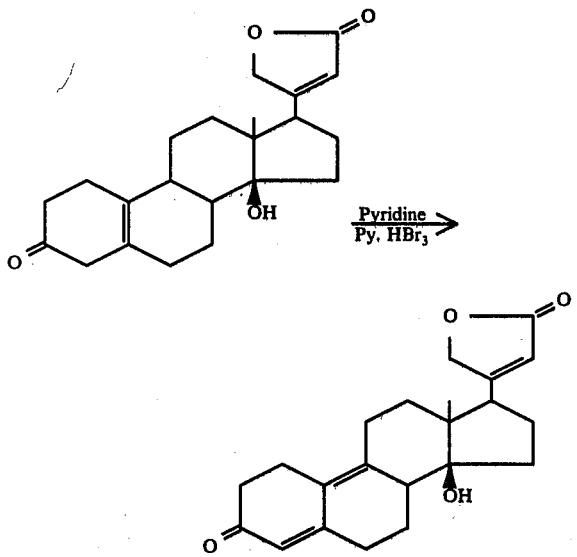

A mixture of 240 mg of 14-hydroxy-3-oxo-19-nor-14β-carda-5(10),20(22)-dienolide, 4.8 ml of pyridine, which had been dried over 4 Å molecular sieves and 216 mg of pyridinium bromide perbromide, was stirred magnetically in the dark under nitrogen for 2 hours and 15 minutes whereupon 4.8 ml of 4% aqueous sodium bisulfite was added. The mixture was stirred for 10 minutes and 12.0 ml of 5% aqueous sodium bicarbonate was added. The mixture was then concentrated three times to 4.8 ml with addition of 4.8 ml of water after each concentration. Subsequent filtration of the resulting suspension, which no longer smelled of pyridine, gave 198 mg of a light brown precipitate, uv(CH₃OH) 217 and 308 mμ. Stirring of 20 mg of the latter precipitate in 1.0 ml of acetone for 15 minutes, followed by addition of 0.5 ml of hexane, filtration, evaporation of the solvents, dissolution of the residue in 0.2 ml of acetone, addition of 5 lots of 0.020 ml of water, subsequent shaking for 1 hour and filtration gave 7 mg of 14-hydroxy-3-oxo-19-nor-14β-carda-4,9(10),20(22)-trienolide, mp 110°-125°, as a white powder.

EXAMPLE 26

A mixture of 6.0 mg of 14-hydroxy-3-ono-19-nor-14β-carda-4,9(10),20(22)-trienolide, 0.9 ml of methylene chloride, 360 mg of zinc dust and 0.3 ml of 90% formic acid were shaken in a nitrogen atmosphere for 168 minutes. Subsequent filtration and evaporation at reduced pressure with intermittent addition of toluene gave a product, which was considered to consist mainly of 14-hydroxy-19-nor-5β,14β-carda-3,9(10),20(22)-trienolide. The thin layer chromatogram of the product had a major spot, which was slightly more polar than that of the analogous 14-hydroxy-19-nor-5β,14β-carda-3,20(22)-dienolide.

When 3 mg of the same starting material was shaken with 0.225 ml of methylene chloride, 90 mg of zinc dust and 0.075 ml of 90% formic acid a greenish solution was obtained within 30 minutes which after shaking overnight turned to light blue. A sample, which was taken after 30 minutes and was then evaporated, had uv 217 (major), and 357 (minor) mμ while the product which was obtained after 16 hours of shaking, subsequent filtration and evaporation had only a maximum in the uv-spectrum at 216.5 mμ. Both the sample and the product did not contain starting material and were considered to contain 14-hydroxy-19-nor 5β,14β-carda-3,9(10),20(22)-trienolide, as evidenced by tlc.

EXAMPLE 27

To a solution, which consisted of 200 mg digitoxigenin and 20.0 ml of tertiary butanol-water 7:3 and was protected by an atmosphere of nitrogen, was added 240 mg of N-bromoacetamide, which had been dried in high vacuum with swirling and exclusion of light. The mixture was then shaken with the exclusion of light for 2 hours at room temperature, whereupon it was left to stand in ice-water for 100 minutes. Tlc analysis of samples taken during the reaction showed that practically no reaction had taken place after 30 minutes, but that after 120 minutes all of the starting material appeared to have been converted to the corresponding 3-ketone. The mixture was then warmed to room temperature and shaken for 30 minutes in the dark under nitrogen with 6.0 g of zinc dust, and then with 240 mg of sodium bicarbonate for 30 minutes. Filtration, addition of 20 ml of water to the filtrate, concentration at reduced pressure to 4 ml, addition of another lot of 20 ml of water followed by concentration to 10 ml and filtration of the resulting suspension gave 177.08 mg of 14-hydroxy-3-oxo-5β,14β-card-20(22)-enolide, mp 194°, 196°-199° C, nmr (CDCl₃,δ) 5.86 (1, broadened S; 22—H), 4.92 (2, incompletely resolved dd; 21—H), 2.56-3.0 (m; 17α—H), 1.01 (3, S; 19—H) and 0.93 (3, S; 18—H) ppm.

EXAMPLE 28

To a mixture of 60 mg of 14-hydroxy-3-oxo-5β,14β-card-20(22)-enolide, 36 glass beads, which had a diameter of 3 mm, 1.8 g of zinc dust, which had been dried at high vacuum for half an hour, and 4.5 ml of methylene chloride, which had been stored over 4 Å molecular sieves, were added 9 lots of 0.54 ml of 90% formic acid each, at time interval of 20 minutes. Each lot was added dropwise with intermittent stirring, and after each addition the mixture was shaken mechanically for 20 minutes. Twenty minutes after the last addition, 3.0 ml of acetone was added and the mixture was shaken again for 20 minutes. Subsequent filtration, addition of 1 N aqueous sodium bicarbonate till the reaction mixture was just alkaline, neutralization of the small excess of alkali with small lots of 2 N aqueous acetic acid, concentration at reduced pressure to 3.0 ml, addition of 3.0 ml of water, another concentration to 3.0 ml and filtration gave 47 mg of a white powder, mp 174°, 176°-178° C. Dissolution of this precipitate in methylene chloride, followed by filtration and concentration at reduced pressure with intermittent addition of hexane and filtration of the resulting suspension gave 40 mg of 3-deoxydigitoxigenin, mp 175°, 177°-179° C, ir(KBr) 3528, 3090, 2940, 2882, 2856, 1785, 1754, 1730, 1719, 1628, 1448, 1375, 1349, 1264, 1188, 1170, 1141, 1120, 1075, 1060, 1030, 1020, 988, 958, 905, 890, 850, 825, 736, and 693 cm⁻¹, nmr (CDCl₃,δ) 5.87(1, broadened S; 22—H), 4.94 (2, partially resolved dd; 21—H), 2.58—2.98 (m; 17α—H), 0.92 (3, S; 19—H) and 0.88 (3, S; 18—H) ppm.

EXAMPLE 29

A mixture of 1.0 g of digoxin, 20 ml of 0.1 N aqueous sulfuric acid and 20 ml of tertiary butanol was shaken in an atmosphere of nitrogen in a water-bath having a temperature of 80° C for 4 hours. The mixture, which had clarified after 1½ hour of shaking, was then cooled in an ice-water bath for 0.5 hours, whereupon 20 ml of distilled water was added and the reaction mixture was concentrated to 40 ml at reduced pressure. Addition of 20 ml of water, followed by two further concentrations to 40 ml with intermittent addition of 20 ml of water gave, after cooling in an ice-water bath for 0.5 hour and filtration, 521 mg of an off-white powder, mp 170, 182°-188° C, the thin layer chromatogram of which showed practically only one spot and was identical with that of digoxigenin.

Treatment of 200 mg of digoxigenin, which had been obtained as described above, with N-bromoacetamide by the procedure, which was very similar to the one described in Example 27 for the oxidation of digitoxigenin, gave, after filtration of the final aqueous suspension, 142.26 mg of a white powder, mp 244°, 246°-248° C, nmr (CDCl$_3$-CD$_3$OD 1:1,$\delta$), 5.93 (1, broadened S; 22—H), 4.93 (2, unresolved dd; 21—H), 4.08 (~1.5, S, changing to a broad multiplet after D$_2$O treatment, impurity ?), 3.17–3.63 (m; 12$\alpha$—H, 17$\alpha$—H; and impurity ?), 1.04 (3, S; 19—H) and 0.83 (3, S; 18—H) ppm. Treatment of an acetylated sample, which was taken from the reaction mixture just before working up, showed that nearly all the starting material had been converted to 3-dehydro-digoxigenin and that besides the very small amount of residual digoxigenin, there was present a somewhat larger amount of the corresponding 3,12-dehydro analog.

EXAMPLE 30

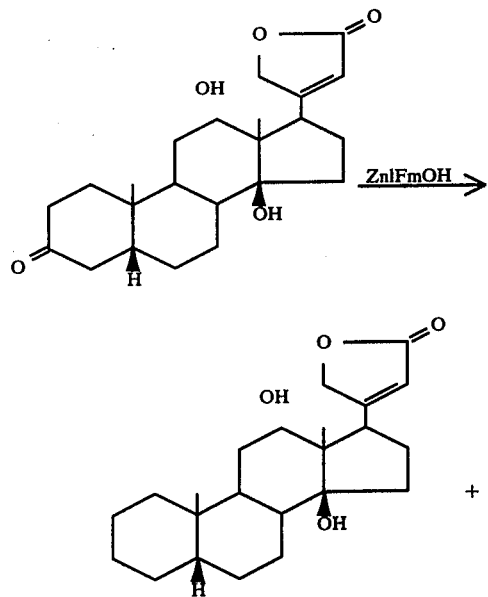

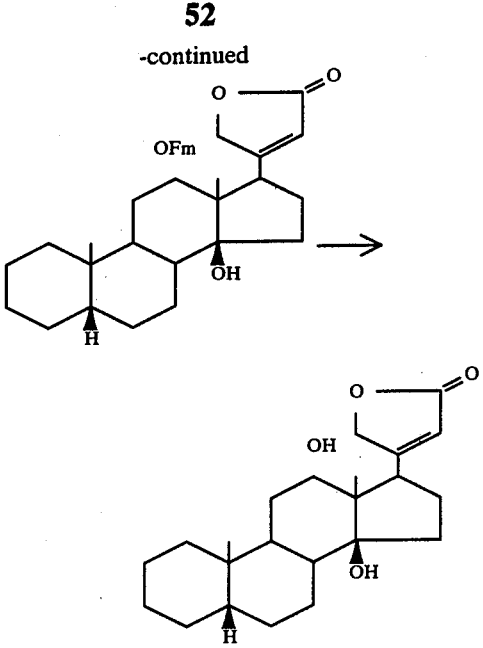

To a mixture of 60.0 mg of 3-dehydrodigoxigenin, 1.2 g of glass beads, which had a diameter of 3 mm, 1.8 g of zinc dust, which had been dried at high vacuum, 4.5 ml of methylene chloride, which had been dried over 4 Å molecular sieves, were added ten lots of 0.060 ml each of 90% formic acid at time intervals of 20 minutes. Each individual lot of formic acid was added dropwise with intermittent swirling. After each addition the mixture was mechanically shaken for 20 minutes. Two hours after the last addition the mixture was externally cooled in ice-water, whereupon 3.0 ml of methanol was added with agitation. The stopper of the reaction flask was firmly fixed and the mixture was shaken in the ice-water for approximately 1½ to 2 hours and was then left to stand in a refrigerator at +5° C for 16 hours. The stopper was then removed carefully to allow a gradual release of the moderate pressure, which can develop during the methanol treatment, the remaining zinc was removed by filtration and the mixture was concentrated 3 times to 1.2 ml with intermittent addition of 6.0 ml each of methanol.

The methanolic solution was then diluted with 4.8 ml of methanol, 12 lots of 0.3 ml of freshly prepared 1 N aqueous sodium bicarbonate were added and the barely alkaline reaction mixture was stirred for 1 hour in an effort to hydrolyze small amounts of 12-formate, which may have formed in the reaction, whereupon 0.45 ml of 2 N aqueous acetic acid was added. The mixture, which was then no longer basic, was concentrated twice to 1.2 ml at reduced pressure with intermittent addition of 1.2 ml each of water. Subsequent filtration gave 44 mg of a white precipitate, which was dissolved in 4.4 ml of acetonemethylene chloride 1:1, briefly stirred with 22.0 mg of diatomaceous earth and filtered. Concentration to 0.44 ml, followed by slow addition of 4.4 ml of hexane to the resulting suspension, which was stirred under nitrogen, 4 to 5 hours of further stirring and filtration gave 36.0 mg of a white precipitate, mp 177°-188° C, which after dissolution in 2.16 ml of methylene chloride, precipitation by slow addition of 2 volumes of hexane, approximately 3 hours of further stirring and filtration gave 33.5 mg of 3-deoxydigoxigenin, mp 194°, 201°, 214°-216° C, ir(KBr) 3496, 3115 (weak, 22—H), 2970, 2950, 2909, 2860, 1785, 1740, 1730, 1632, 1447, 1388, 1338, 1300, 1278, 1251, 1200, 1171, 1110, 1171, 1029, 1018, 988, 962, 950, 891, 860, 826, 736, 693 and 661 cm$^1$, nmr(CD$_3$OD,$\delta$) 590 (1, broadened S; 22—H), 4.94 (2, partially resolved d, 21—H), 3.1–3.6 (m, 12$\alpha$—H, 17$\alpha$—H, methanol), 0.97 (3, S; 19—H) and 0.80 (3, S; 18—H) ppm.

EXAMPLE 31

Treatment of 200 mg of digoxigenin, which had been obtained as described in Example 29, with N-bromoacetamide by the procedure, which was very similar to the one described in Example 29 except that reaction mixture was left to stand at room temperature, i.e. between 25 and 27° C, for 5 days, before the zinc was added, gave, after filtration of the final aqueous suspension, 100 mg of a white powder mp, 248°, 251°-253° C, nmr (CDCl$_3$–CD$_3$OD, $\delta$) 5.95 (1, broadened S; 22—H), 4.88 (2, broadened S; 21—H), 3.92–4.38 (1, m; 17$\alpha$—H) and 1.12 (6, S; 18—H, 19—H) ppm, consisting essentially of 3,12-dehydrodigoxigenin. The product of another reaction, which was obtained by a procedure, which was essentially the same as the one described above, had ir(KBr) 3440, 3140, (22—H) 3080, 2930, 2860, 1770, 1735, 1690, 1622, 1440, 1380, 1348, 1300, 1280, 1265, 1213, 1176, 1140, 1115, 1102, 1096, 1060, 1030, 996, 964, 945, 891, 839, 860, 810, 772 and 696 cm$^{-1}$.

EXAMPLE 32

Subjection of 60 mg of the 3,12-dioxo-14-hydroxy-5$\beta$,14$\beta$-card-20(22)-enolide, which had been prepared as described in the preceding Example, to the reaction and purification conditions, which are described in Example 28 for the conversion of digitoxigenone to 3-deoxydigitoxigenin, gave 47.13 mg of a white powder, consisting essentially of 12-oxo-3-deoxydigitoxigenin dissolution of the latter product in acetone, followed by slow addition of 6 volumes of water and filtration gave 27.0 mg of a precipitate, which after dissolution in acetone followed by precipitation with 11 volumes of water yielded 21.79 mg of 12-oxo-3-deoxydigitoxigenin, mp 218°, 219°-220.5° C, ir (KBr) 3470, 3108 (weak 22—H), 2978, 2925, 2864, 2842, 1794, 1738, 1700 (12-ketone), 1618, 1450, 1420, 1405, 1384, 1364, 1312, 1296, 1276, 1240, 1220, 1175, 1155, 1133, 1064, 1025, 986, 948, 898, 858, 835, 810, 736 and 700 cm$^{-1}$.

EXAMPLE 33

A mixture of 200 mg of 19-hydroxy 17$\beta$-pivaloxy androsta-4,7-dien-3-one, 15.0 ml of methylene chloride, 12.0 g of zinc dust and 5.0 ml of 90% formic acid was shaken overnight, when 130 ml of toluene and 20 ml of water were added. After some further shaking, the mixture was filtered, the zinc was washed with ethylacetate and the combined filtrates were extracted several times with water. Evaporation followed by precipitation gave a white precipitate, mp 144°-146° C, nmr (CDCl$_3$,$\delta$), 8.17 (1, S; OCHO), 5.06–5.83 (3, m; 3—H, 4—H, 7—H), 4.53–4.90 (1, m; 17$\alpha$—H), 4.21 (2, broadened S; 19—H), 1.20 (9, S; trimethylacetate) and 0.70 (3, S; 18—H) ppm m/e 400 (molecular ion), 371, 354 and 398, considered to consist of 19-formyloxy-17$\beta$-pivaloxy-5$\beta$-androsta-3,7-diene. Tlc analysis of a sample taken after 30 minutes showed no starting material, 19-hydroxy-17$\beta$-pivaloxy-5$\beta$-androsta-3,7-diene as the major product and a product considered to be the 5$\alpha$-isomer of the latter.

EXAMPLE 34

Treatment of 2.50 mg of 19-hydroxy-20$\beta$-pivaloxy-pregna-4,6,8(14)-trien-3-one, with zinc dust and 90% formic acid by a procedure, which was very similar to the one used in the preceding Example except that the amount of zinc was reduced from 60 to 30 parts per part of starting material, followed by chromatography of the crude product on silica gel G coated glass plates, with ethylacetate benzene 1:4 as the eluant, gave a major fraction, which after recrystallization from methylene chloride-hexane, yielded 102.58 mg of a yellowish precipitate, mp 227°-229° C. Subsequent recrystallization from methylene chloride-methanol gave a white crystalline solid, nmr (CDCl$_3$,$\delta$) 8.1 (1, S; 19-formate), 5.69 (2, broadened S; 3—H, 4—H, double bond in position 3, adjacent to 5,7-cyclopropyl group), 4.67-5.20 (1, m; 20$\alpha$—H), 4.23 (2, broadened S; 19—H), 1.20 (9, S; trimethylacetate), 1.14 (3, d; 21—H) and 0.87 (3, S; 18—H) ppm, ir (KBr) 3000, 2942, 2918, 2858, 1715, 1470, 1445, 1388, 1368, 1277, 1155, 1058, 1028, 933, 860, 766 and 682 cm$^{-1}$, m/e 426 (molecular ion), 398, 396, 380, 378, 368, 325, and 311, considered to be 5,7-cyclo-19-formyloxy-20$\beta$-pivaloxypregna-3,8(14)-diene. A product which was similarly prepared in an another reaction had u.v. (MeOH) 218 m$\mu$.

Treatment of 37.5 mg of the above 19-formate with 0.25 N alcoholic potassium hydroxide under nitrogen for 16 hours at room temperature gave, after neutralization with glacial acetic acid, concentration at reduced pressure with intermittent addition of ethyl acetate and water, and filtration of the aqueous suspension, which was finally obtained, 34 mg of a white precipitate. Dissolution of the latter in methylene chloride, followed by concentration with intermittent addition of hexane and filtration gave 19.4 mg of a compound considered to be 5,7-cyclo-19-hydroxy-20$\beta$-pivaloxy-pregna-3,8(14)-diene, nmr (CDCl$_3$,$\delta$)5.73 (2, broadened S; 3—H, 4—H, double bond in position 3 adjacent to 5.7-cyclopropyl group?), 4.67–5.17 (1, m; 3.63 (2, dd; 19—H)) 1.20 (9, S, trimethylacetate), and 0.83 (3, S; H—18) ppm, m/e 398 (molecular ion), and 297 (m—101).

EXAMPLE 35

A mixture of 200 mg of 5$\alpha$-androsta-3,17-dione, 15.0 ml of toluene, 6.0 g of zinc dust and 5.0 ml of 90% formic acid was agitated for one hour, whereupon it was filtered. Evaporation of the filtrate at reduced pressure with intermittent addition of toluene, followed by dissolution of the resulting white precipitate in methanol, slow addition of water and filtration gave 5$\alpha$-androst-17-one, mp 124°-125° C, nmr (CDCl$_3$) 0.84 (3, S; 19—H) and 0.80 (3, S; 18—H) ppm, ir (KBr) 2956, 2904, 2840, 2820, 1740, 1562, 1442, 1052, 1002 and 825 cm$^{-1}$.

EXAMPLE 36

A mixture of 300 mg of hydrocortisone, 22.5 ml of methylene chloride, 18g of zinc dust and 7.5 ml of 90% formic acid was agitated under nitrogen for 30 minutes, whereupon one volume each of toluene and water were added and the mixture was shaken for a further 30 minutes. Filtration, washing of the zinc residue with ethyl acetate, three extractions of the combined filtrate and washings with half a volume of water and evaporation gave 271 mg of a white solid, which was chromatographed on neutral alumina. Elution with ethyl acetate, followed by dissolution of the major fraction in methylene chloride, concentration with intermittent addition of hexane and filtration of the resulting suspension gave a product, which on the basis of tlc analysis and nmr-spectroscopy was considered to contain 11β,17α, 21-trihydroxy-5β-pregn-3-en-20-one as the major and the corresponding 5α-isomer as the minor component. The UV-spectrum of a sample which was prepared under essentially identical conditions had UV (MEOH) 209 mμ.

EXAMPLE 37

Treatment of 150 mg prednisolone acetate with zinc, formic acid and methylene chloride in a nitrogen atmosphere under conditions which were similar to those described for the 3-deoxygenation of hydrocortisone in the preceding example except that the amount of formic acid was reduced to 10 ml per gram of steroid, gave a white solid as the crude product.

Several precipitations of the product from hexanemethylene chloride gave 78 mg of a white solid, which on the basis of its nmr-spectrum and tlc-analysis was considered to contain a mixture of 21-acetoxy-11β,17α-dihydroxy-5β-pregn-1,3-diene and the corresponding 5α-hydrogen and 2,4-diene isomers.

EXAMPLE 38

A mixture of 250 mg of progesterone, 7.5 g of zinc dust, 18.75 ml of methylene chloride and 6.25 ml of 90% formic acid was shaken at room temperature for 18 hours, whereupon it was worked up by the procedure described in Example 36. Concentration of a solution of the crude product in methylene chloride with intermittent addition of pentane gave 99.18 mg of 5β-pregn-3-en-20-one, mp 135°–136.5°, 139.5° C, nmr (CDCl$_3$,δ) 5.5 (2, broadened dd; 3—H, 3—H, 4—H), 2.12 (3, S; 21—H) 0.96 (3, S; 19—H), 0.77 (trace, S; 19—H of 5α-isomer?) and 0.61 (3, S; 18—H) ppm.

EXAMPLE 39

Treatment of 5β-pregnan-3,20-dione, which contained a trace of an impurity considered to be the 5α-isomer, under deoxygenation conditions, which were very similar to those described in the preceding Example, gave 5β-pregnan-20-one as a white powder, mp 111°–113° C, nmr (CDCl$_3$, δ), 2.10 (3,S; 21—H), 0.93 (3, S; 19—H), 0.78 (trace, S; 19—H of 5α-isomer) and 0.61 (3, S; 18—H) ppm.

EXAMPLE 40

A mixture of 10 mg of stigmasta-4,22-dien-3-one, 300 mg of zinc dust, 1.0 ml of methylene chloride and 0.250 ml of 90% formic acid was shaken at room temperature. Tlc-analysis showed that already after 15 minutes all starting material had been converted to a considerably less polar material which appeared as a single spot and was considered to consist of 5β-stigmasta-3,22-diene as the major product and possibly contained the corresponding 5α-isomer as the minor product.

Tlc-analysis for which the samples were neutralized with aqueous sodium bicarbonate and extracted with ethyl acetate, also showed that the stigmastadienone is converted to the same product when instead of the formic acid, cyanoacetic, glycolic 85% lactic, salicylic or methacrylic acid was used. The conversion was complete in 15 minutes when the cyanoacetic acid was used. It was complete in 16 hours when the glycolic and the 85% lactic acid were used, but it remained incomplete in the reactions employing the salicylic and methacrylic acid.

EXAMPLE 41

A mixture of 200 mg of 16-dehydroprogesterone, 15 ml of toluene, 6.0 g of zinc dust and 1.0 ml of 90% formic acid was shaken for 0.5 hours, whereupon it was filtered and evaporated with intermittent additional of hexane. Precipitation of the crude product, which was obtained as a white solid, from hexane gave 20α-hydroxy-5β-pregna-3,16-diene, mp 118°–120° C, nmr (CDCl$_3$δ) 5.15–5,88 (3, m; 3—H, 4—H, 16—H), 4.57-4.10 (1, m; 20β—H), 1.28 (3, d; 21—H), 0.98 (3, S; 19—H) and 0.88 (3, S, 19—H) ppm. The hexane mother liquors still contained much of the above product and also a minor amount of a product considered to be the corresponding 5α-isomer, as evidenced by tlc analysis.

EXAMPLE 42

A mixture of 200 mg of 16-dehydroprogesterone, 15.0 ml of methylene chloride, 6.0 g of zinc dust and 0.2 ml of 90% formic acid was shaken for 2 hours, whereupon it was filtered. Concentration at reduced pressure with intermittent addition of hexane gave a residue, which was chromatographed on silica gel G coated glass plates using ethyl acetate-benzene, 1:7 as the eluant. Recrystallization of the fraction which contained the major product and was more polar than the starting material, from methylene chloride-hexane gave 36.3 mg of 20α-hydroxy-pregna-4,16-dien-3-one, mp 147, 154°–159° C, nmr (CDCl$_3$,δ), 5.73 (1, broadened S; 4—H), 5.55–5.80 (1, m; 16—H) and 4.08–4.67 (1, m; 20β—H), 1.24 (3, d; 21—H), 1.23 (3, S; 19—H) and 0.95 (3, S; 18—H) ppm. Tlc-analysis indicated that besides the latter compound the crude product was composed of 20α-hydroxy-5β-pregna-3,16-diene and 16-dehydroprogesterone and that these compounds were present in an approximate ratio of 10:1:30, respectively.

EXAMPLE 43

A mixture of 200 mg of 3β-acetoxy-pregna-5,16-dien-20-one, 15.0 ml of toluene, 6.0 g of zinc dust and 1.0 ml of 90% formic acid was shaken for 30 minutes, whereupon it was filtered. Concentration of the filtrate at reduced pressure to a small volume, followed by addition of hexane, further concentration and filtration gave 131.0 mg of a white precipitate, mp 127°–134° C. Slow addition of half a volume of water to a solution of latter precipitate in 13.0 ml of methanol yielded, after filtration of the resulting suspension, 67.0 mg of 3β-acetoxy-20β-hydroxypregna-5,16-diene, mp 141°–142° C, nmr (CDCl$_3$,δ), 5.57–5.78 (1, m or broadened S; 16—H), 5.10-5.50 (1, m; 5—H), 4.13–4.92 (2, m; 3α—H, 20β—H), 2.03 (3, S; OCOCH$_3$), 1.33 (3,d; 21—H), 1.07 (3, S, 19—H) and 0.93 (3, S; 18—H) ppm. From the mother liquor of the above precipitate 27.0 mg of a second crop of product was collected. The mother liquor of the latter consisted only of polar impurities, which appeared to be already present in the commercial starting material.

When 200.0 mg of the above starting material was subjected to reaction conditions, which were identical to those described above except that the formic acid was substituted by 2.0 ml of glacial acetic acid and the reaction time was prolonged to one hour, a crude product was obtained which still contained, besides the 20α-alcohol and the polar impurities, a small amount of the starting material. Precipitation from methanol-water 100:50, followed by precipitation from methylene chloride-hexane 5:25, gave 77.0 mg of 3β-acetoxy-20α-hydroxypregna-5,16-diene, mp 141°–142° C, the nmr spectrum of which was identical to the one of the product obtained above by reduction with zinc in the presence of formic acid.

EXAMPLE 44

A mixture 200.0 mg of 16-dehydropregnenolone acetate oxime, 15.0 ml of methylene chloride, 6.0 g of zinc dust and 1.0 ml of 90% formic acid was shaken for 30 minutes, whereupon it was filtered.

The precipitate containing the residual zinc was washed with 20.0 ml of methylene chloride-acetic acid 5:1. The filtrate and the washings were combined and evaporated at reduced pressure yielding a residue containing 3β-acetoxy-20ξ-amino-pregna-5,16-diene as evidenced by tlc.

Treatment of nine tenths of the above product with 0.36 ml of acetic anhydride and 0.72 ml of pyridine for 16 hours, followed by addition of 10.2 ml of water and filtration gave 134.0 mg of a white electrostatic precipitate, which was recrystallized repeatedly from methylene chloride-hexane and also from methanol-water yielding white powders, mp 145°–150° C, nmr (CDCl$_3$, δ) 5.23–5.73 (2, m; 16—H, 5—H), 4.33–4.93 (2, m; 3α—H, 20 ξ—H), 2.03 (3, S; OCOCH$_3$), 1.97 (3, S; NHCOCH$_3$), 1.27 (3, d with small shoulders; 21—H), 1.07 (3,S; 19—H) and 0.90 (3, S; 18—H) ppm, considered to be mixtures of 20α-(acetylamino)-3β-acetoxy-pregna-5,16-diene and the corresponding 20β-isomer.

EXAMPLE 45

The compound employed in this example was prepared according to the teachings of Example 30, namely, 3-deoxydigoxigenin. This compound was subjected to further testing according to the procedures described relative to Table I and yielded the following results: at a molar concentration of $7.6 \times 10^{-6}$, it increased the contractility by 50% (contractility being as defined in Table I and the accompanying disclosure). At a molar concentration of $6.8 \times 10^{-5}$, it caused a 50% inhibition of 80 ATP-ase (as defined in Table I and the accompanying disclosure). Thus, the compound had comparable biological and inotropic effects and the ATP-ase inhibition as the 19-deoxygenated steroid acetyl-strophanthidin. A further useful property of this compound in the anitropic test is it was much less arrhythomogenic relative to the anitropic activity than digoxin from which it is derived by 3-deoxygenation.

It will be understood that various and modifications may be made to the above-described disclosure without departing from the spirit and scope of the invention. In this respect, a preferred group of compounds are those having the formula:

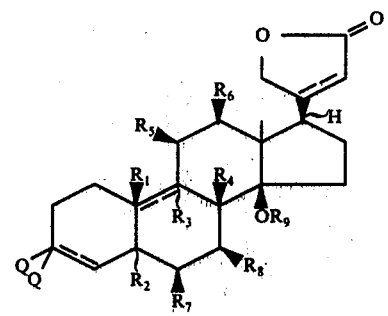

wherein Q is selected from the group consisting of H; tritium or deuterium; R$_1$ is selected from the group consisting of CH$_2$OH; CH$_2$—OAcyl; CH$_3$; H; or 5(10)=; R$_2$ is selected from α or β-H or α or β-tritium; R$_3$, R$_4$, R$_8$ are H or OH; R$_5$ is H, OH, tritium or deuterium; R$_6$ is OH or =O; R$_7$ is H; and R$_9$ is O=C—H, or O=C—C.

I claim:

1. A 19-oxygenated steroid compound of the formula

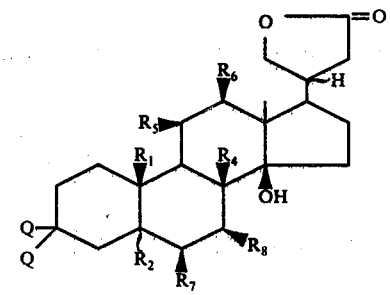

wherein

Q is selected from the group consisting of hydrogen, deuterium and tritium;

R$_1$ is selected from the group consisting of CH$_2$OH, the tetrahydropyranyl ether of CH$_2$OH, the p-toluenesulfonate of CH$_2$OH, CHO, CH$_2$Br, COOH, COOCH$_3$ and CH$_2$O-acyl, wherein acyl is formyl, acetyl, heptafluoropropionyl, pivalyl, heminalonyl or hemisuccinyl;

R$_2$ is α or β—H;

R$_4$, R$_5$, R$_7$ and R$_8$ are each selected from the group consisting of H and OH;

R$_6$ is H, OH or =O; and the Δ1, Δ2, Δ3, Δ4, Δ5(6), Δ6, Δ7, Δ9(11), Δ11 and Δ20(22) dehydro analogues thereof.

2. The compound of claim 1 wherein the compound is a saturated 19-oxygenated compound.

3. A 19-methyl steroid compound of the formula

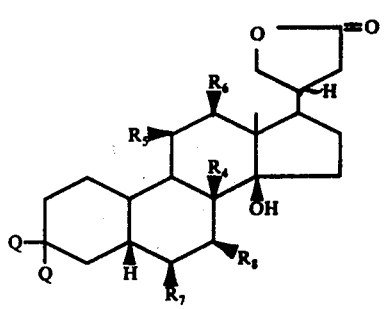

wherein

Q is selected from the group consisting of deuterium and tritium;

$R_4$, $R_5$, $R_7$ and $R_8$ are each selected from the group consisting of H and OH; and $R_6$ is selected from the group consisting of H, OH, =O, acetoxy and formyloxy with the proviso that when $R_6$ is H, Q is other than H; and the Δ1, Δ2, Δ3, Δ4, Δ5(6), Δ6, Δ7, Δ9(11), Δ11 and Δ20(22) dehydro analogues thereof.

4. The compound of claim 3 wherein the compound is a saturated compound.

5. A 19-nor steroid compound of the formula

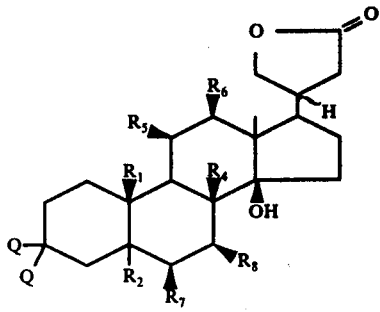

wherein

Q is selected from the group consisting of hydrogen, deuterium and tritium;

$R_1$ and $R_2$ are each H, or $R_1$ together with $R_2$ is a 5(10) double bond;

$R_4$, $R_5$, $R_7$ and $R_8$ are each selected from the group consisting of H and OH;

$R_6$ is selected from the group consisting of H, OH and =O; and the Δ1, Δ2, Δ3, Δ4, Δ5(6), Δ6, Δ7, Δ9(11), Δ11 and Δ20(22) dehydro analogues thereof.

6. The compound of claim 5 wherein the compound is a saturated compound.

7. A compound having the formula

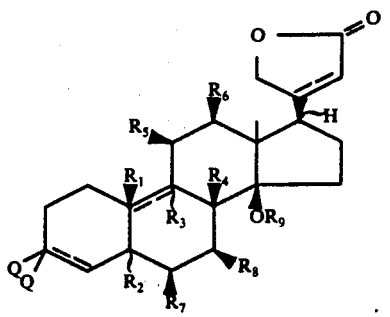

where Q is selected from the group consisting of H, tritium or deuterium; $R_1$ is selected from the group consisting of $CH_2OH$; $CH_2$-OAcyl; $COOHCOOCH_3$; $CH_3$; H; or together with $R_2$ is a 5(10) double bond; $R_2$ is selected from the group consisting of α-H, β-H, α-tritium, β-tritium, α-deuterium and β-deuterium; $R_3$ and $R_4$ are H or OH; $R_5$ is H or OH; $R_6$ is H, OH or =O; $R_7$ is H; $R_8$ is H and $R_9$ is H.

8. A compound as defined in claim 7, said compound having the formula

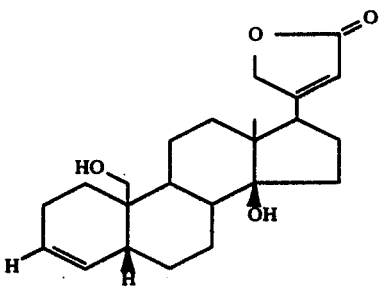

9. A compound as defined in claim 7, said compound having the formula

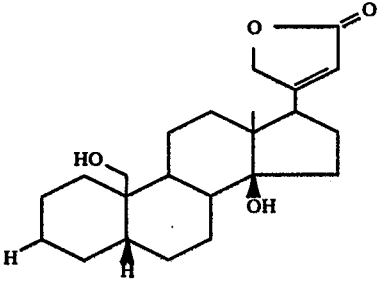

10. A compound as defined in claim 7, said compound being 3-deoxydigoxigenin.

11. A compound as defined in claim 7 wherein the compound is 14,19-dihydroxy-5β,14β,20-cardanolide, 3-deoxy-19-nor digitoxigenin, 14-hydroxy-12-oxo-5β,14β-card-20(22)-enolide, 14-hydroxy-19-nor-14β-carda-5(10),20(22)-dienolide, 14-hydroxy-19-nor-5β,14β-carda-3,20(22)-dienolide, 14,19-dihydroxy-5α,14β-carda-3,20(22)-dienolide, 19-methoxycarbonyl-14-hydroxy-5β,14β-carda-3,20(22)-dienolide, or 19-carboxy-14-hydroxy-5β,14β-carda-3,20(22)-dienolide.

12. A compound as defined in claim 11, said compound comprising the 19-formate of the 19-hydroxy compounds.

13. A process of preparing a compound of the formula

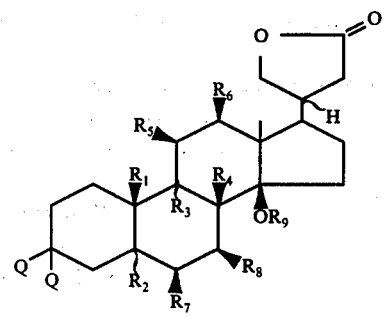

(I)

wherein
Q is selected from the group consisting of hydrogen, deuterium or tritium; $R_1$ is selected from the group consisting of $CH_2OH$, $CH_2OCH$, $CH_2OCCH_3$, $CH_2OCCF_2CF_2CF_3$,
$CH_2OCC(CH_3)_3$, $CH_2OCCH_2CO_2H$, $CH_2OC(CH_2)_2CO_2H$, $CH_2OSO_2$—⟨⟩—$CH_3$, CHO, $CH_2Br$, $CH_3$, $CO_2H$, $CO_2CH_3$, OH, H;

$R_2$ is selected from the group consisting of β-H, β-deuterium, β-tritium, α-H, α-deuterium, α-tritium, and β-OH; $R_3$ is selected from the group consisting of β-H and β-OH;

$R_4$ is selected from the group consisting of β-H and β-OH;

$R_5$, $R_6$, $R_7$, $R_8$ are selected from the group consisting of H, =O,

OH, $OCH$, $OCCH_3$, and $OCC(CH_3)_3$, $R_9$ is selected from the group consisting of H, $CH_3$—$\overset{O}{\underset{\|}{C}}$—, $H\overset{O}{\underset{\|}{C}}$—;

and in the case of compounds having an additional bond at the 5,8,9 or 10-position the substituents $R_2$, $R_4$, $R_1$ or $R_3$ respectively are absent; and the Δ1, Δ2, Δ3, Δ4, Δ5(6), Δ7, Δ8, Δ9(11), Δ11, and Δ20(22) dehydro analogues thereof comprising:
treating a 3β,14β-dihydroxy-cardenolide with an agent selected from the group consisting of N-bromoacetamide and molecular oxygen in the presence of platinum to obtain the corresponding 3-oxo-14β-hydroxy-cardenolide;
further treating said 3-oxo-14β-hydroxy-cardenolide with ethane-dithiol to obtain the corresponding 3-thioketal; and
then treating said 3-thioketal with Raney nickel to obtain the corresponding compound of Formula I.

14. A process of preparing a compound of the formula

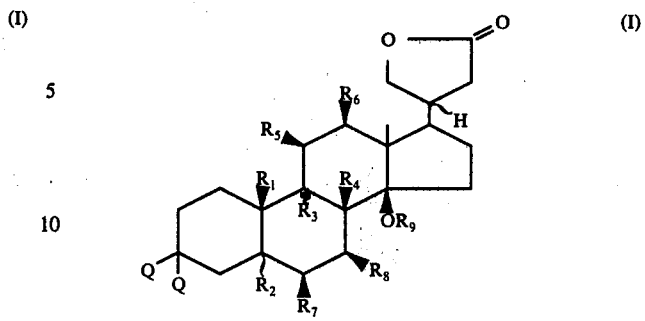

(I)

wherein Q is selected from the group consisting of hydrogen, deuterium or tritium; $R_1$ is selected from the group consisting of $CH_2OH$, $CH_2OCH$, $CH_2OCCH_3$, $CH_2OCCF_2CF_2CF_3$,
$CH_2OCC(CH_3)_3$, $CH_2OCCH_2CO_2H$, $CH_2OC(CH_2)_2CO_2H$, $CH_2OSO_2$—⟨⟩—$CH_3$, CHO, $CH_2Br$, $CH_3$, $CO_2H$, $CO_2CH_3$, OH, H;

$R_2$ is selected from the group consisting of β-H, β-deuterium, β-tritium, α—H, α—deuterium, α-tritium, and β-OH; $R_3$ is selected from the group consisting of β-H and β-OH; $R_4$ is selected from the group consisting of β-H and β-OH; $R_5$, $R_6$, $R_7$, $R_8$ are selected from the group consisting of H, =O, OH, $OCH$, $OCCH_3$, and $OCC(CH_3)_3$, $R_9$ is selected from the group consisting of H, $CH_3$—$\overset{O}{\underset{\|}{C}}$—, $H\overset{O}{\underset{\|}{C}}$—;

and in the case of compounds having an additional bond at the 5,8,9 or 10-position the substituents $R_2$, $R_4$, $R_1$ or $R_3$ respectively are absent; and the Δ1, Δ2, Δ3, Δ4, Δ5(6), Δ7, Δ8, Δ9(11), Δ11, and Δ20(22) dehydro analogues thereof comprising:
treating a 3β,14β-dihydroxy-cardenolide with an agent selected from the group consisting of N-bromoacetamide and molecular oxygen in the presence of platinum to obtain the corresponding 3-oxo-14β-hydroxy-cardenolide with tosylhydrazine to obtain the corresponding 3-tosylhydrazone; and
treating said corresponding 3-tosylhydrazone compound with an agent selected from the group consisting of sodium borohydride and sodium cyanoborohydride to obtain the corresponding compound of Formula I.

15. A process of preparing a compound of the formula

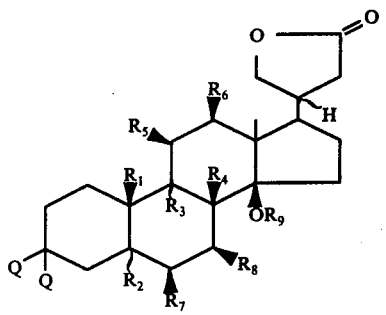
(I)

wherein
Q is selected from the group consisting of hydrogen, deuterium or tritium; $R_1$ is selected from the group consisting of $CH_2OH$, $CH_2OCH$ (with =O), $CH_2OCCH_3$ (with =O), $CH_2OCCF_2CF_2CF_3$ (with =O),
$CH_2OCC(CH_3)_3$ (with =O), $CH_2OCCH_2CO_2H$ (with =O), $CH_2OC(CH_2)_2CO_2H$ (with =O),

$CH_3$, CHO, $CH_2Br$,
$CH_3$, $CO_2H$, $CO_2CH_3$, OH, H;

$R_2$ is selected from the group consisting of $\beta$-H, $\beta$-deuterium,
$\beta$-tritium, $\alpha$-H, $\alpha$-deuterium, $\alpha$-tritium, and $\beta$-OH;
$R_3$ is selected from the group consisting of $\beta$-H and $\beta$-OH;
$R_4$ is selected from the group consisting of $\beta$-H and $\beta$-OH;
$R_5$, $R_6$, $R_7$, $R_8$ are selected from the group consisting of H, =O, OH, OCH (=O), OCCH$_3$ (=O), and OCC(CH$_3$)$_3$ (=O), $R_9$ is selected from the group consisting of H, $CH_3-\overset{O}{\underset{\|}{C}}-$, $H\overset{O}{\underset{\|}{C}}-$;

and in the case of compounds having an additional bond at the 5,8,9 or 10-position the substituents $R_2$, $R_4$, $R_1$ or $R_3$ respectively are absent; and the $\Delta 1$, $\Delta 2$, $\Delta 3$, $\Delta 4$, $\Delta 5(6)$, $\Delta 7$, $\Delta 8$, $\Delta 9(11)$, $\Delta 11$, and $\Delta 20(22)$ dehydro analogues thereof comprising:
treating a $3\beta,14\beta$-dihydroxy-cardenolide with an agent selected from the group consisting of N-bromoacetamide and molecular oxygen in the presence of platinum to obtain the corresponding 3-oxo-14$\beta$-hydroxy-cardenolide; and
treating said 3-oxo-14$\beta$-hydroxy-cardenolide with zinc and an aqueous carboxylic acid to obtain the corresponding compound of Formula I.

16. A process as defined in claim 13 in which the $3\beta,14\beta$-dihydroxy cardenolide used as the starting material possesses an additional hydroxy group in the 19-position or in the B or C-ring.

17. A process as defined in claim 16 in which the hydroxy group is in the B and C-ring and is situated in the $\beta$-position.

18. A process as defined in claim 15, in which the $3\beta,14\beta$-dihydroxy cardenolide used as the starting material possesses an additional double bond in the 4, 5(10), 5(6) or 9(10) position.

19. A process as defined in claim 15 in which the oxidation of the $3\beta,14\beta$-dihydroxy cardenolide to the 3-oxo-14$\beta$-hydroxy cardenolide is carried out with N-bromoacetamide in aqueous tert. butanol.

20. A process as defined in claim 19 in which after the completion of the oxidation the reaction mixture is treated with zinc dust and then with sodium bicarbonate.

21. A process as defined in claim 19, in which the starting material is a $3\beta,5,14\beta$-trihydroxy cardenolide, the reaction mixture is treated successively with zinc and sodium bicarbonate and is filtered free of solvent and following which the residue obtained is dehydrated to the corresponding 3-oxo-14$\beta$-hydroxy-carda-4,20(22)-dienolide.

22. A process as defined in claim 21, in which the dehydration is carried out with aqueous hydrochloric acid.

23. A process as defined in claim 21, in which the dehydration is carried out with hydrochloric acid at or below room temperature.

24. A process as defined in claim 21, in which the starting material is strophanthidin and the reaction is carried out in the dark.

25. A process as defined in claim 24, in which the 3,19-dioxo-14-hydroxy-14$\beta$-carda-4,20(22)-dienolide is obtained.

26. A process as defined in claim 15, in which digoxygenin is converted to 3-dehydrodigoxigenin.

27. A process as defined in claim 15, in which digoxigenin is converted to 3,12-dehydro digoxigenin.

28. A process as defined in claim 15, in which the oxidation of the compound is carried out in the dark, and the resulting mixture is subsequently shaken in the presence of light to yield 19-carboxy-3-oxo-5,14-dihydroxy-5$\beta$,14$\beta$-carda-20(22)-enolide.

29. A process as defined in claim 28, in which after irradiation, the reaction mixture is treated successively with zinc and sodium bicarbonate, filtered, and the filtrate obtained is heated in the presence of isopropanol between 50° to 100° C to yield 3-oxo-14-hydroxy-19-nor-14$\beta$-carda-5,(10),20(22)dienolide.

30. A process as defined in claim 29, in which the irradiated reaction mixture is treated successively with sodium thiosulfate and sodium bicarbonate, acidified with acetic acid, extracted with chloroform-methanol and the combined organic extracts are evaporated to yield the 3-oxo-14-hydroxy-19-nor-14$\beta$-carda-5,(10),-20(22)dienolide.

31. A process wherein a compound of the formula

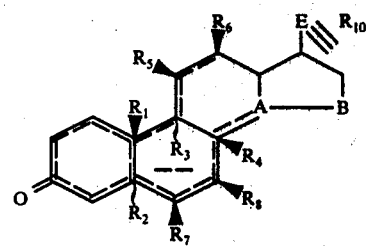

(II)

wherein R₁ through R₈, R₁₀ and E are as defined hereinafter, is treated with zinc and a carboxylic acid in a minimum amount of solvent, to form a compound of the formula

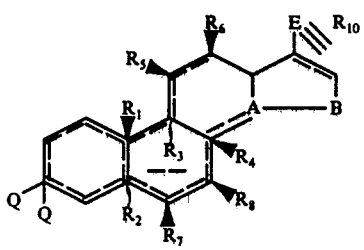

wherein Q, R₁ through R₈, and the dotted and wavy lines are as defined in claim 15; R₁₀ is selected from the group consisting of H, OH and

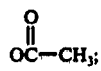

and wherein E is selected from the group consisting of

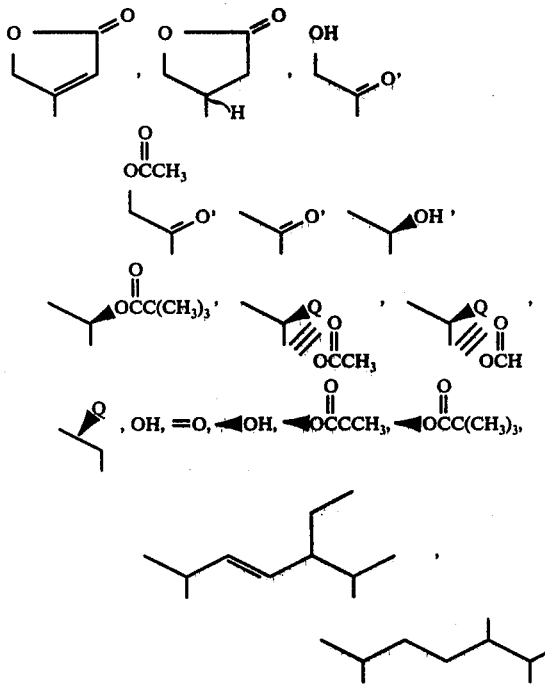

CO₂H, CHO, CH₂OH, and wherein A-B is selected from the group consisting of from C(β-OH)-CH₂,

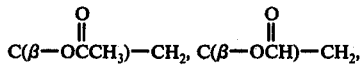

C=CH, C(α—OH)-CH₂, C(β-OH)-CHBr, C(β—H)—CH₂, C(α—H)—CH₂,

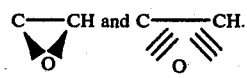

32. A process as defined in claim 31 wherein formic acid, cyanoacetic acid, glycolic acid or lactic acid is used as said carboxylic acid.

33. A process as defined in claim 31 including removing the oxygen of the 3-keto group of a saturated 3-keto cardenolide by said treatement with zinc and an aqueous carboxylic acid.

34. A process as defined in claim 31 including removing the oxygen of the 3-keto group of a 3-keto cardenolide having a double bond in a conjugated position to the keto group by said treatment with zinc and an aqueous carboxylic acid.

35. A process as defined in claim 31 in which the ketone which is treated with zinc and an aqueous carboxylic acid has a double bond in the 5(10) or 5(6) position.

36. A process as defined in claim 33, in which said treatment includes the addition of formic acid dropwise with intermittent shaking to the reaction mixture containing a cold solvent, zinc and the 3-ketone compound.

37. A process as defined in claim 33, in which said treatment includes the addition of formic acid dropwise with intermittent shaking to the reaction mixture containing a cold solvent, zinc and the 3-ketone compound.

38. A process as defined in claim 37, wherein the solvent is methylene chloride, toluene or tetrahydrofuran and said treatment is carried out at or below room temperature.

39. A process as defined in claim 37, in which a 16-dehydro-20-keto group is present in addition to the 3-keto group and in which the 16-dehydro-20-keto group is treated with a carboxylic acid in a solvent to reduce it to a 16-dehydro-20α-hydroxy group.

40. A process as defined in claim 39, in which the reduction of the 16-dehydro-20 keto group to the 16-dehydro-20α-hydroxy group is carried out selectively before the deoxygenation of the 3-keto group by said treatment with zinc and a carboxylic acid.

41. A process as defined in claim 39, in which the 4-ene-3-one group is deoxygenated by said treatment with zinc and a carboxylic acid and subsequently the 16-dehydro-20 ketone group is reduced.

42. A process as defined in claim 39, in which 16-dehydro-pregnenolone acetate is reduced to 3β-acetoxy-20-hydroxy-pregna-5,16α-diene by said treatment with zinc and a carboxylic acid.

43. A process as defined in claim 42, in which the oxime of said pregnenolone acetate is reduced to the corresponding 20ξ-amino-pregna-5,16-diene by said treatment with zinc and a carboxylic acid.

44. A process for preparing 3-deoxy-cannogenol, which comprises treating strophantidin with N-bromoacetamide followed by treatment with an agent selected from the group consisting of zinc and aqueous sodium thiosulfate, to obtain strophantidone; treating said last-named compound with an acidic agent selected from the group consisting of acetic acid and aqueous hydrochloric acid to obtain 3,19-dioxo-14-hydroxy-14β-carda-4,20(22)-dienolide; treating said last-named compound with sodium borohydride to obtain 14,19-dihydorxy-3-oxo-14β-carda-4,20(22)-dienolide; treating said last-named compound with hydrogen in the presence of a catalyst and t-butylamine to obtain 14,19-dihydroxy-3-oxo-5β,14β-carda-20(22)-enolide; treating said last-named compound with zinc and aqueous carboxylic acid followed by treatment with sodium bicarbonate, and isolating the 3-deoxy-cannogenol, so produced.

45. A process as defined in claim 44, wherein the carboxylic acid is formic acid.

46. A process as defined in claim 44, wherein the acidic agent is acetic acid and treatment therewith is at a temperature between 60° and 120° C at a temperature of −20° C.

47. A process as defined in claim 44 wherein the acidic agent is hydrochloric acid and the treatment therewith is at a temperature of between −20° C and room temperature.

48. In a process of deoxygenating 4-en-3-one steroid compounds, the improvement comprising treating the ketone with zinc and a carboxylic acid in the presence of a solvent.

49. In a process as defined in claim 48 wherein the amount of carboxylic acid is between 1–25 parts of the carboxylic acid per part of the ketone.

50. A process as defined in claim 48 wherein the carboxylic acid is a member selected from the group consisting of formic acid and acetic acid.

51. A compound as defined in claim 11, said compound comprising the 19-acylate of the 19-hydroxy compounds.

* * * * *